US008977506B2

(12) United States Patent
Anderson

(10) Patent No.: US 8,977,506 B2
(45) Date of Patent: *Mar. 10, 2015

(54) SYSTEMS AND METHODS FOR DETECTING BIOLOGICAL FEATURES

(75) Inventor: Glenda G. Anderson, San Jose, CA (US)

(73) Assignee: Response Genetics, Inc., Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/418,991

(22) Filed: Mar. 13, 2012

(65) Prior Publication Data

US 2012/0215514 A1 Aug. 23, 2012

Related U.S. Application Data

(63) Continuation of application No. 10/954,443, filed on Sep. 29, 2004, and a continuation-in-part of application No. 10/861,216, filed on Jun. 4, 2004, now abandoned, and a continuation-in-part of application (Continued)

(51) Int. Cl.
*G01N 33/48* (2006.01)
*G01N 31/00* (2006.01)

(Continued)

(52) U.S. Cl.
CPC ............... *G06F 19/24* (2013.01); *G06F 19/18* (2013.01); *G06F 19/20* (2013.01)
USPC .................... 702/19; 702/22; 703/11; 703/12

(58) Field of Classification Search
CPC ................... C12Q 2600/112; C12Q 2600/158; C12Q 1/6886; A63B 2230/00
See application file for complete search history.

(56) References Cited

U.S. PATENT DOCUMENTS 6,263,287 B1 7/2001 Zheng et al.
6,303,301 B1 10/2001 Mack et al.

(Continued)

FOREIGN PATENT DOCUMENTS

EP 1037158 A2 9/2000
EP 1043676 A2 10/2000

(Continued)

OTHER PUBLICATIONS

Golub et al. (Science, 1999, 286, 531-537).*
Nguyen et al. (Bioinformatics, 2002, 18(1), 39-50).*
*American Heritage College Dictionary*. Third Edition, 1993, Houghton Mifflin Company, New York. p. 786.
Anderson et al., 1984, "Global Approaches to Quantitative Analysis of Gene-Expression Patterns Observed by Use of Two-Dimensional Gel Electrophoresis," Clin. Chem. 30. 2031-2036.
Arch-Ferrer et al., 2003, "Genetic expression of thymidylate synthase, dihydropyrimidine dehydrogenase and thymidine phosphorylase and its clinical correlation in gastric adenocarcinoma," ASCO abstr 1101.
Australian Patent Office Search Report, dated May 8, 2007.
Australian Patent Office Written Opinion, dated May 8, 2007.
Ben-Dor et al., 2000, "Tissue Classification with Gene Expression Profiles," Journal of Computational Biology 7: 559-583.

(Continued)

*Primary Examiner* — Larry D Riggs, II
(74) *Attorney, Agent, or Firm* — Morgan, Lewis & Bockius LLP

(57) ABSTRACT

A computer having a memory stores instructions for receiving data. The data comprises one or more characteristics for each cellular constituent in a plurality of cellular constituents that have been measured in a test organism of a species or a test biological specimen from an organism of the species. The memory further stores instructions for computing a model in a plurality of models, wherein the model is characterized by a model score that represents the likelihood of a biological feature in the test organism or the test biological specimen. Computation of the model comprises determining the model score using one or more characteristics for one or more cellular constituents in the plurality of cellular constituents. The memory also stores instructions for repeating the instructions for computing one or more times, thereby computing the plurality of models. The memory also stores instructions for communicating computed model scores.

18 Claims, 3 Drawing Sheets

Related U.S. Application Data

No. 10/861,177, filed on Jun. 4, 2004, now Pat. No. 8,321,137.

(60) Provisional application No. 60/577,416, filed on Jun. 5, 2004, provisional application No. 60/507,381, filed on Sep. 29, 2003, provisional application No. 60/507,445, filed on Sep. 29, 2003.

(51) Int. Cl.

| | | |
|---|---|---|
| G06G 7/48 | (2006.01) | |
| G06G 7/58 | (2006.01) | |
| G06F 19/24 | (2011.01) | |
| G06F 19/18 | (2011.01) | |
| G06F 19/20 | (2011.01) | |

(56) References Cited

U.S. PATENT DOCUMENTS

| | | | |
|---|---|---|---|
| 6,344,316 | B1 | 2/2002 | Lockhart et al. |
| 6,351,712 | B1 | 2/2002 | Stoughton et al. |
| 6,389,305 | B1 | 5/2002 | Deban et al. |
| 6,420,108 | B2 | 7/2002 | Mack et al. |
| 6,453,241 | B1 | 9/2002 | Bassett, Jr. et al. |
| 6,468,476 | B1 | 10/2002 | Friend et al. |
| 6,502,039 | B1 | 12/2002 | Theilhaber et al. |
| 6,505,125 | B1 | 1/2003 | Ho |
| 6,647,341 | B1 | 11/2003 | Golub et al. |
| 7,774,143 | B2 * | 8/2010 | Khan et al. ............ 702/19 |
| 2001/0044414 | A1 | 11/2001 | Clark et al. |
| 2001/0049393 | A1 | 12/2001 | Coller et al. |
| 2002/0110820 | A1 | 8/2002 | Ramaswamy et al. |
| 2002/0115070 | A1 | 8/2002 | Tamayo et al. |
| 2002/0155480 | A1 | 10/2002 | Golub et al. |
| 2003/0013097 | A1 | 1/2003 | Welsh et al. |
| 2003/0017481 | A1 | 1/2003 | Golub et al. |
| 2003/0073083 | A1 | 4/2003 | Tamayo et al. |
| 2003/0084043 | A1 | 5/2003 | Acharya et al. |
| 2003/0087865 | A1 | 5/2003 | Golub et al. |
| 2003/0134300 | A1 | 7/2003 | Golub et al. |
| 2003/0138793 | A1 | 7/2003 | Su et al. |
| 2003/0152980 | A1 | 8/2003 | Golub et al. |
| 2003/0194701 | A1 | 10/2003 | Golub et al. |
| 2003/0211531 | A1 | 11/2003 | Hampton et al. |
| 2003/0215835 | A1 | 11/2003 | Sun et al. |
| 2003/0219760 | A1 | 11/2003 | Gordon et al. |
| 2003/0225526 | A1 | 12/2003 | Golub et al. |
| 2004/0009489 | A1 | 1/2004 | Golub et al. |
| 2004/0009495 | A1 | 1/2004 | O'Malley et al. |
| 2004/0010481 | A1 | 1/2004 | Mani et al. |
| 2004/0058340 | A1 | 3/2004 | Dai et al. |
| 2004/0098367 | A1 | 5/2004 | Tamayo et al. |
| 2004/0110193 | A1 | 6/2004 | Castle et al. |
| 2005/0069863 | A1 | 3/2005 | Anderson et al. |
| 2005/0071143 | A1 | 3/2005 | Tran et al. |

FOREIGN PATENT DOCUMENTS

| | | |
|---|---|---|
| EP | 1274463 A2 | 1/2003 |
| EP | 1339872 A2 | 9/2003 |
| WO | WO 97/12247 | 4/1997 |
| WO | WO 02/24956 A2 | 3/2002 |
| WO | WO 02/061144 A2 | 8/2002 |
| WO | WO 02/101357 A2 | 12/2002 |
| WO | WO 03/008552 A2 | 1/2003 |
| WO | WO 03/021229 A2 | 3/2003 |
| WO | WO 03/029273 A2 | 4/2003 |
| WO | WO 03/041562 A2 | 5/2003 |
| WO | WO 03/053223 A2 | 7/2003 |
| WO | WO 2005/033877 A2 | 4/2005 |
| WO | WO 2005/042760 A2 | 5/2005 |
| WO | WO 2005 084171 | 9/2005 |

OTHER PUBLICATIONS

Bhattacharjee et al,. 2001, "Classification of human lung carcinomas by mRNA expression profiling reveals distinct adenocarcinoma subclasses," Proc. Natl. Acad. Sci. USA 98: 13790-13795.

Blanchette et al., 2002, "Discovery of Regulatory Elements by a Computational Method for Phylogenetic Footprinting," Genome Research 12(5) : 739-748.

Bol et al., 2003, "Proliferation markers and DNA content analysis in urinary bladder TaT1 urothelial cell carcinomas: identification of subgroups with low and high stage progression risks", J. Clin. Pathol. 56: 447-452.

Brown et al., 2001, "Universal trees based on large combined protein sequence data sets," Nature Genetics 28: 281-285.

Caldas et al., 2002, "The Molecular Outlook," Nature 415: 484-485.

Carlson et al., 1998, "An algorithm combining age, total prostate-specific antigen (PSA), and percent free PSA to predict prostate cancre: results on 4298 cases." Urology 52(3): 455-461.

Chang et al., 2003. "Gene expression profiling for the prediction of therapeutic response to docetaxel in patients with breast cancer", Lancet 362:362-369.

Chang et al., 2002, "Gene Expression Profiles for Docetaxel Chemosensitivity," PeerView Press abstr 1700.

Clarke and Granek, 2003. "Rank order metrics for quantifying the association of sequence features with gene regulation," Bioinformatics 19: 212-218.

Claverie, 1999, "Computational methods for the identification of differential and coordinated gene expression," Human Molecular Genetics 8: 1821-1832.

Cobleigh et al., 2003, "Tumor gene expression predicts distant disease-free survival (DDFS) in breast cancer patients with 10 or more positive nodes: High throughput RT-PCR assay of paraffin-embedded tumor tissues," ASCO abstr 3415.

Dzeroski et al., 2000, "Using data mining and OLAP to discover patterns in a database of patients with Y-chromosome deletions", Proc. AMIA Symp. 2000:215-219.

Golub et al., 1999, "Molecular Classification of Cancer: Class Discovery and Class Prediction by Gene Expression Monitoring," Science 286: 531-537.

Gordon et al., 2002,"Translation of Microarray Data into Clinically Relevant Cancer Diagnostic Tests Using Gene Expression Ratios in Lung Cancer and Mesothelioma," Cancer Research 62, 4963-4967.

Gordon et al., 2003, "Using Gene Expression Ratios to Predict Outcome Among Patients With Mesothelioma," J. National Cancer Institute 95: 598-605.

Gruvberger et al., 2001, "Estrogen Receptor Status in Breast Cancer Is Associated with Remarkably Distinct Gene Expression Patterns," Cancer Research 61, 5979-5984.

Hayes et al., 2003, "Validation of lung adneocareinoma subtypes by mRNA expression profiling," ASCO abstr 2526.

Heydorn et al., 2000, "Quantification of biofilm structures by the novel computer program Comstat," Microbiology 146: 2395-2407.

Heyer et al., 1999, "Exploring expression data: identification and analysis of coexpressed genes," Genome Research 9: 1106-1115.

Hobday et al., 2003, "Molecular markers in metastatic gastrointestinal neuroendocrine tumors," ASCO abstr 1078.

Hussain et al., 2003, "Gene expression profiles of taxotere treated prostate cancer cells by cDNA microarray analysis," ASCO abstr 1677.

Ikeda et al., 2003, "Chemo sensitivity-related genes of breast cancer detected by DNA microarray," ASCO abstr 34.

International Search Report, dated Jun. 27, 2005 for PCT/US04/31835.

International Search Report, dated Jun. 27, 2005 for PCT/US04/32006.

International Search Report, dated Jun. 27, 2005 for PCT/US04/32007.

Jiang et al., 2000. "Construction of Evolutionary Tree Models for Renal Cell Carcinoma from Comparative Genomic Hybridization Data," Cancer Research 60: 6503-6509.

Kwon et al., 2003, "Gene expression analaysis of colorectal cancer examined by cDNA microarray," ASCO abstr 1104.

Leichman et al., 2003, "Expression of thymidylate synthase (TS), glutathione-and excision-repair-related genes in primary esophageal cancer (PEC): The results of an exploratory analysis for patients (pts)

(56) References Cited

OTHER PUBLICATIONS treated with oxaliplatin (OXP), protracted infusion (PI) 5-fluorouracil (5FU) and radiation (XRT)," ASCO abstr 1054.
Lenz et al.. 2003, "Gene expression profile in normal tissue predicts pelvic recurrence in patients with rectal cancer treated with adjuvant chemoradiation therapy," ASCO abstr 1185.
Li et al., 2001, "Model-based analysis of oligonucleotide arrays: model validation, design issues and standard error application", Genome Biology 2(8). research0032.1-0032.11.
Long et al., 2003, "Reduced PTEN expression correlates with advanced stage disease in breast cancer," ASCO abstr 3410.
McGeoch et al.. 2000, "Toward a Comprehensive Phylogeny for Mammalian and Avian Herpes viruses," Journal of Virology 74: 10401-10406.
Office Action dated Oct. 1 2010, for U.S. Appl. No. 10/861,216.
Office Action for U.S. Appl. No. 10/861,177, dated Apr. 27, 2010.
Office Action for U.S. Appl. No. 10/861,177, dated Apr. 28, 2009.
Office Action for U.S. Appl. No. 10/861,177, dated Oct. 28, 2008.
Office Action for U.S. Appl. No. 10./861,177, dated Dec. 26. 2007.
Office Action for U.S. Appl. No. 10/861,177, dated Apr. 18, 2007.
Office Action for U.S. Appl. No. 10/861,177, dated Nov. 29, 2006.
Office Action for U.S. Appl. No. 10/861,216, dated Mar. 3. 2009.
Office Action, dated Jul. 31, 2006, in U.S. Appl. No. 10/861,216.
Office Action, dated Jun. 4, 2008, in U.S. Appl. No. 10/861,216.
Office Action, dated Jun. 8, 2007, in U.S. Appl. No. 10/861,216.
Office Action, dated May 11, 2007, in U.S. Appl. No. 10/954,443.
Office Action, dated Nov. 2, 2007, in U.S. Appl. No. 10/861,216.
Office Action, dated Sep. 29, 2006, in U.S. Appl. No. 10/861,216.
Pepe et al. 2003 "Selecting Differentially Expressed Genes from Microarray Experiments," Biometrics 59: 133-142.
Perou et al, 1999, "Distinctive gene expression patterns in human mammary epithelial cells and breast cancers," Proc. Natl. Acad. Sci. USA 96: 9212-9217.
Pusztai et al., 2003. "Emerging Science: Prospective validation of gene expression profiling-based prediction of complete pathologic response to neoadjuvant paclitaxel/FAC chemotherapy in breast cancer," ASCO abstr I.
Ramaswamy et al., 2001. "Multiclass cancer diagnosis using tumor gene expression signatures," Proc. Natl. Acad. Sci. USA 98(26):15149-15154.
Ramaswamy et al., 2002, "A molecular signature of metastasis in primary solid tumors," Nature Genetics 33, 49-54.
Ramaswamy et al., 2002, "DNA Microarrays in Clinical Oncology," J. Clinical Oncology 20, 1932-1941.
Richer et al., 2001, "Differential Gene Regulation by the Two Progesterone Receptor Isoforms in Human Breast Cancer Cells," J. Biological Chemistry 277, 5209-5218.
Rosell-Costa et al., 2003, "ERCC1 and RRM1 expression predicts survival: A genetic analysis of a Spanish Lung Cancer Group trial of gemcitabine (gem)/cisplatin (cis) versus gem/cis/vinorelbine (vrb) vs sequential doublets of gem/vrb and vrb/ifosfamide (ifos) in stage IV non-small-cell lung cancer (NSCLC)," ASCO abstr 2590.
Schneider et al., 2003, "Accumulation of uPA-PAI-1 complexes inside the tumour cells is associated with axillary nodal invasion in progesterone-receptor-positive early breast cancer," British Journal of Cancer 88: 96-101.
Shipp et al., 2002, "Diffuse Large B-cell Lymphoma Outcome Prediction by Gene-Expression Profiling and Supervised Machine Learning," Nature Medicine 8: 68-74.
Simon, 2003, "Diagnostic and prognostic prediction using gene expression profiles in high-dimensional microarray data," British Journal of Cancer 89: 1599-1604.
Singhal et al., 2003, "Gene Expression Profiling of Malignant Mesothelioma," Clinical Cancer Research 9, 3080-3097.
Slonim et al., 2000, "Class Prediction and Discovery Using Gene Expression Data," ACM 2000 1: 263-272.
Song et al., 2003. "Prognostic significance of $p53$, Rb, EGFR, and c-erbB2 genes in curatively resected gastric cancer," ASCO abstr 1056.
Soule et al., 2003, "Predicting response to neoadjuvant chemotherapy in invasive breast cancer: Gene expression profiling of paraffin-embedded core biopsy tissue," ASCO abstr 3466.
Su et al., 2001, "Molecular Classification of Human Carcinomas by Use of Gene Expression Signatures," Cancer Research 61, 7388-7393.
Supplemental European Search Report, dated Nov. 13. 2007, for EP 04816896.7.
Supplemental European Search Report, dated Nov. 13, 2007, for EP 04821586.7.
Supplemental European Search Report. dated Nov. 2, 2007, for EP 04789181.7.
Takano et al., 2003, "Identitication of paclitaxel-resistance related genes by differential display using cDNA microarray in ovarian cancer cell lines," ASCO abstr 1856.
Tamayo et al., 1999, "Interpreting patterns of gene expression with self-organizing maps: Methods and application to hematopoietic differentiation," Proc. Natl. Acad. Sci. USA 96: 2906-2912.
Tamayo et al., 1999, "Interpreting Patterns of Gene Expression with Self-Organizing Maps: Methods and Application to Hemapoietic Differentiation." Proc, Natl. Acad. Sci. USA 96: 2907-2912.
Terashima et al., 2003, "Detection of chemoresistance-related gene in human gastric cancer using DNA microarray," ASCO abstr 1161.
Van 'T Veer et al., 2002, "Gene expression profiling predicts clinical outcome of breast cancer," Nature 415: 530-536.
Welsh et al., 2001, "Analysis of Gene Expression Identifies Candidate Markers and Pharmacological Targets in Prostate Cancer," Cancer Research 61: 5974-5978.
Wilson et al. 2002, "Differential Gene Expression Patterns in HER2/ *neu*-Positive and -Negative Breast Cancer Cell Lines and Tissues," American Journal of Pathology 161: 1171-1185.
Zhang et al., 1997, "Gene Expression Profiles in Normal and Cancer Cells," Science 276: 1268-1272.
Khan, et al., "Classification and Diagnostic Prediction of Cancer using Gene Expression Profiling and Artificial Neutral Networks", Nature Medicine, vol. 7, No. 6; pp. 673-679 (Jun. 2001).

\* cited by examiner

SYSTEMS AND METHODS FOR DETECTING BIOLOGICAL FEATURES

CROSS-REFERENCE TO RELATED APPLICATIONS

This application is a continuation of U.S. patent application Ser. No. 10/954,443 filed on Sep. 29, 2004, which claims benefit, under 35 U.S.C. §119(e), of U.S. Provisional Patent Application No. 60/577,416 filed on Jun. 5, 2004, each of which is incorporated herein, by reference, in its entirety. Application Ser. No. 10/954,443 also claims benefit, under 35 U.S.C. §119(e), of U.S. Provisional Patent Application No. 60/507,381 filed on Sep. 29, 2003 which is incorporated herein, by reference, in its entirety. Application Ser. No. 10/954,443 also claims benefit, under 35 U.S.C. §119(e), of U.S. Provisional Patent Application No. 60/507,445 filed on Sep. 29, 2003 which is incorporated herein, by reference, in its entirety. Application Ser. No. 10/954,443 is a continuation-in-part of U.S. patent application Ser. No. 10/861,216, now abandoned, filed on Jun. 4, 2004, which is incorporated herein, by reference, in its entirety. Application Ser. No. 10/954,443 is also a continuation-in-part of U.S. patent application Ser. No. 10/861,177, filed on Jun. 4, 2004, now issued as U.S. Pat. No. 8,321,137, which is incorporated herein, by reference, in its entirety.

1. FIELD OF THE INVENTION

The field of this invention relates to computer systems and methods for identifying biological features, such as disease, in biological specimens.

2. BACKGROUND OF THE INVENTION

A first step in rationally treating disease is to assess the patient against a classification of diseases, the results being used to determine what kind of disease the patient has and to predict the person's response to various therapies. The effectiveness of the process depends on the quality of the classification. At least in the case of cancer, the advent of microarray methods to analyze DNA, RNA or proteins from tumor cells has started to refine and improve the classification of cancer cells. See, for example, Golub et al., 1999, Science 286, p. 531.

Further, van't Veer et al., 2002, Nature 415, p. 530, illustrates how such "molecular profiling" is improving cancer classification. Van't Veer et al. shows that the results of gene-expression profiling of breast tumors, carried out after they had been surgically removed, can be used to predict which patients will develop clinical metastasis (the spread of the tumor to other sites, where secondary tumors develop). Treatment for individual breast cancer patients is chosen according to various criteria, such as the extent of tumor spread (which involves determining tumor size), whether cancer cells have spread to the auxiliary lymph nodes and how many nodes are involved, and whether distant clinical metastases are present. In women with no evidence of metastasis, the mainstay of treatment aimed at curing the disease is the removal of the tumor and radiotherapy. Unfortunately some of these patients later develop clinical metastasis. Thus, there is a need to identify women who, after surgery, will require further ("adjuvant") therapy for the microscopic deposits of cancer cells that may have already spread from the primary tumor. See, for example, Caldas and Aparicio, 2002, Nature 415, p. 484; and Goldhirsch et al. 1998, J. Natl. Cancer Inst. 90, p. 1601.

Adjuvant therapy uses pharmaceutical agents, such as oestrogen modulators or cytotoxic drugs that reach cancer cells through the bloodstream. Such treatments frequently have toxic side effects. Identifying women who might need such treatment has traditionally relied on various clinical and histopathological indicators (e.g., patient's age, degree to which the cancer cells resemble their normal counterparts, the 'tumor grade', and whether the cancer cells express the oestrogen receptor). Even taken together, however, these indicators are only poorly predictive. So, to save a sizable but small percentage of lives, many patients who would have been cured by surgery and radiotherapy alone go on to receive unnecessary and toxic adjuvant treatment.

The results of van't Veer et al., 2002, Nature 415, p. 530 as well as other studies are beginning to be used in classification schemes that attempt to characterize a biological specimen (e.g. tumor) from a patient into plurality of biological sample classes (e.g., breast cancer requiring adjuvant therapy versus breast cancer that does not require adjuvant therapy). A number of clinical trials, funded by companies and organizations such as the Avon Foundation, Millennium Pharmaceuticals, the European Organization for Research and Treatment of Cancer, and the National Cancer Institute, are presently underway to discover and validate such classification schemes. See, for example, Branca, 2003, Science 300, p. 238.

A number of biological classification schemes are available for breast cancer. For example, Ramaswamy et al., 2003, Nature Genetics 33, p. 49 provides a gene-expression signature that distinguishes primary from metastatic adenocarcinomas. Su et al., 2001, Cancer Research 61, p. 7388, describe the use of large-scale RNA profiling and supervised machine-learning algorithms to construct a first-generation molecular classification scheme for identifying carcinomas of the prostate, breast, lung ovary, colorectum, kidney, pancreas, bladder/ureter, and gastroesophagus. The Su et al., molecular classification scheme is useful in diagnosing metastatic cancers in which the origin of the primary tumor has not been determined. Wilson et al., 2002, American Journal of Pathology 161, provides an expression signature characteristic of HER2/neu positive tissue that is correlated with reduced survival of node-positive breast cancer patients. Richer et al., 2002, The Journal of Biological Chemistry 277, p. 5209, provides a genetic signature for human breast cancer cells that are over-expressing progesterone receptor-A (PR-A) and a genetic signature for human breast cancer cells that are over-expressing progesterone receptor-B (PR-B). As indicated by Richer et al., 2002, an excess of one or the other PR isoforms can result in tumors with different prognostic and hormone-responsiveness profiles from tumors that have equimolar levels of the two PR isoforms. Gruvberger et al., 2001, Cancer Research 61, p. 5979, provides a molecular classification based on DNA microarray data that can discriminate tumors based on estrogen receptor status.

The biological classification schemes outlined above are just a sampling of the many biological classification schemes that are available for breast cancer. Further, breast cancer, represents just one of many biological classifications of interest. Other representative biological classifications include a diagnosis of cancer generally and, even more generally, a diagnosis of a disease. One problem with each of these aforementioned biological classification schemes is that they each require specialized input (e.g., formatted microarray data). Thus, in an effort to characterize a biological specimen, the specialized input and output of each biological classification scheme must be deciphered. Because of such obstacles, medical care professionals typically use only a limited subset, at most, of such biological classification schemes.

Thus, given the above background, what is needed in the art are improved methods for making biological classification schemes available for classifying specimens into biological classes.

Discussion or citation of a reference herein will not be construed as an admission that such reference is prior art to the present invention.

3. SUMMARY OF THE INVENTION

A first embodiment of the present invention provides a computer having a central processing unit and a memory coupled to the central processing unit. The memory stores instructions for receiving data, wherein the data comprises one or more characteristics for each cellular constituent in a plurality of cellular constituents that have been measured in a test organism of a species or a test biological specimen from an organism of the species. The memory further stores instructions for computing a model in a plurality of models, wherein the model is characterized by a model score that represents the absence or presence of a biological feature in the test organism or the test biological specimen. Computation of the model comprises determining the model score using one or more characteristics for one or more cellular constituents in the plurality of cellular constituents. The memory further comprises instructions for repeating the instructions for computing one or more times, thereby computing the plurality of models. Also stored in the memory are instructions for communicating each of the computed model scores.

In some embodiments, two or more model scores are communicated by the instructions for communicating and each model score in these two or more model scores corresponds to a different model in the plurality of models. In some embodiments, five or more model scores are communicated by the instructions for communicating and each model score in the five or more model scores corresponds to a different model in the plurality of models.

In some embodiments, the instructions for receiving data comprise instructions for receiving the data from a remote computer over a wide area network such as the Internet. In some embodiments, the instructions for communicating comprise instructions for transmitting each model score to a remote computer over a wide area network such as the Internet.

In some embodiments, the test organism or the test biological specimen is deemed to have the biological feature represented by a model in the plurality of models when the model score is in a first range of values and not to have the biological feature represented by the model when the model score is in a second range of values. In some embodiments, the biological feature is a disease such as cancer (e.g., breast cancer, lung cancer, prostate cancer, colorectal cancer, ovarian cancer, bladder cancer, gastric cancer, or rectal cancer, etc.)

In some embodiments, the plurality of models comprises a first model characterized by a first model score and a second model characterized by a second model score and an identity of a cellular constituent whose one or more characteristics is used to compute the first model score is different than an identity of a cellular constituent whose one or more characteristics is used to compute the second model score.

In some embodiments, a characteristic in the one or more characteristics for one or more cellular constituents used to determine the model score for a model in the plurality of models comprises an abundance of the one or more cellular constituents in the test organism of the species or the test biological specimen from an organism of the species. In some instances, the species is human. In some instances, the test biological specimen is a biopsy or other form of sample from a tumor, blood, bone, a breast, a lung, a prostate, a colorectum, an ovary, a bladder, a stomach, or a rectum.

In some embodiments, the one or more characteristics comprises cellular constituent abundance and the data comprises cellular constituent abundances of at least one hundred, at least five hundred, at least five thousand, or between one thousand and twenty thousand cellular constituents in the test organism of the species or said the biological specimen from the organism of the species. In some embodiments, a cellular constituent in the plurality of cellular constituents is mRNA, cRNA or cDNA.

In some embodiments of the present invention, a cellular constituent in the one or more cellular constituents is a nucleic acid or a ribonucleic acid and a characteristic in the one or more characteristics of the cellular constituent is obtained by measuring a transcriptional state of all or a portion of the cellular constituent in the test organism or the test biological specimen. In some embodiments, a cellular constituent in the one or more cellular constituents is a protein and a characteristic in the one or more characteristics of the cellular constituent is obtained by measuring a translational state of the cellular constituent in the test organism or the test biological specimen. In some embodiments, a characteristic in the one or more characteristics of a cellular constituent in the plurality of cellular constituents is determined using isotope-coded affinity tagging followed by tandem mass spectrometry analysis of the cellular constituent using a sample obtained from the test organism or the test biological specimen. In some embodiments, a characteristic in the one or more characteristics of a cellular constituent in the plurality of cellular constituents is determined by measuring an activity or a post-translational modification of the cellular constituent in a sample obtained from the test organism or in the test biological specimen.

In some embodiments, the biological feature is sensitivity to a drug. In some embodiments, the plurality of models for which model scores are computed by instances of the instructions for computing collectively represent the presence or absence of two or more biological features. In some embodiments, each biological feature in the two or more biological features is a cancer origin. In some embodiments, the two or more biological features comprise a first disease and a second disease.

In some embodiments, the plurality of models for which model scores are computed by instances of the instructions for computing collectively represent the presence or absence of five or more biological features. In some instances, each of the five or more biological features represents a different cancer origin. In some instances, the five or more biological features comprise a first disease and a second disease.

In some embodiments, the plurality of models for which model scores are computed by instances of the instructions for computing collectively represent the presence or absence of between two and twenty biological features. In some embodiments, each biological feature in the between two and twenty biological features is a cancer origin. In some embodiments, the between two and twenty biological features comprise a first disease and a second disease.

Another aspect of the invention comprises a computer having a central processing unit and a memory coupled to the central processing unit. The memory stores instructions for receiving data. The data comprises one or more characteristics for each cellular constituent in a plurality of cellular constituents that have been measured in a test organism of a species or a test biological specimen from an organism of the species. The memory further stores (ii) instructions for computing a plurality of models. Each model in the plurality of models is characterized by a model score that represents the absence or presence of a biological feature in the test organism or the test biological specimen. Computation of a respective model in the plurality of models comprises determining the model score associated with the respective model using one or more characteristics for one or more cellular constituents in the plurality of cellular constituents. The memory further stores instructions for communicating each model score computed in an instance of the instructions for computing.

Still another aspect of the invention comprises a computer program product for use in conjunction with a computer system. The computer program product comprises a computer readable storage medium and a computer program mechanism embedded therein. The computer program mechanism comprises instructions for receiving data. The data comprises one or more characteristics for each cellular constituent in a plurality of cellular constituents that have been measured in a test organism of a species or a test biological specimen from an organism of the species. The computer program mechanism further comprises instructions for computing a model in a plurality of models. The model is characterized by a model score that represents the absence or presence of a biological feature in the test organism or the test biological specimen and computation of the model comprises determining the model score using one or more characteristics for one or more cellular constituents in the plurality of cellular constituents. The computer program product further comprises instructions for repeating the instructions for computing one or more times, thereby computing the plurality of models. Still further, the computer program product comprises instructions for communicating each model score computed in an instance of the instructions for computing.

Another aspect of the invention provides a computer program product for use in conjunction with a computer system. The computer program product comprises a computer readable storage medium and a computer program mechanism embedded therein. The computer program mechanism comprises instructions for receiving data. The data comprises one or more characteristics for each cellular constituent in a plurality of cellular constituents that have been measured in a test organism of a species or a test biological specimen from an organism of the species. The computer program mechanism further comprises instructions for computing a plurality of models. Each model in the plurality of models is characterized by a model score that represents the absence or presence of a biological feature in the test organism or the test biological specimen and computation of a respective model in the plurality of models comprises determining the model score associated with the respective model using one or more characteristics for one or more cellular constituents in the plurality of cellular constituents. The computer program mechanism further comprises instructions for communicating each model score computed in an instance of the instructions for computing.

Another aspect of the present invention comprises a method in which data is obtained. The data comprises one or more characteristics for each cellular constituent in a plurality of cellular constituents that have been measured in a test organism of a species or a test biological specimen from an organism of the species. The method further comprises computing a model in a plurality of models. The model is characterized by a model score that represents the absence or presence of a biological feature in the test organism or the test biological specimen. Computation of the model comprises determining the model score using one or more characteristics for one or more cellular constituents in the plurality of cellular constituents. The method further comprises repeating the computing one or more times thereby computing the plurality of models. The method further comprises communicating each model score computed in an instance of the computing.

Still another aspect of the invention comprises receiving data. The data comprises one or more characteristics for each cellular constituent in a plurality of cellular constituents that have been measured in a test organism of a species or a test biological specimen from an organism of the species. A plurality of models is computed. Each model in the plurality of models is characterized by a model score that represents the absence or presence of a biological feature in the test organism or the test biological specimen and computation of a respective model in said plurality of models comprises determining the model score associated with the respective model using one or more characteristics for one or more cellular constituents in the plurality of cellular constituents. Then, each model score computed in an instance of computing is communicated.

Still another aspect of the invention provides a computer having a central processing unit and a memory, coupled to the central processing unit. The memory stores instructions for sending data. The data comprises one or more characteristics for each cellular constituent in a plurality of cellular constituents that have been measured in a test organism of a species or a test biological specimen from an organism of the species. The memory further stores instructions for receiving a plurality of model scores. Each model score corresponds to a model in a plurality of models. Each model in the plurality of models is characterized by a model score that represents the absence or presence of a biological feature in the test organism or the test biological specimen and computation of the model comprises determining the model score using one or more characteristics for one or more cellular constituents in the plurality of cellular constituents.

Another aspect of the present invention provides a computer comprising a central processing unit and a memory coupled to the central processing unit. The memory stores instructions for receiving data, wherein the data comprises one or more aspects of the biological state of each cellular constituent in a plurality of cellular constituents that have been measured in a test organism of a species or a test biological specimen from an organism of the species. The memory further stores instructions for computing a model in a plurality of models. The instructions for computing produce a model characterization for the model that indicates whether the test organism of the species or the test biological specimen from the organism of the species is a member of a biological sample class. The instructions for computing the model comprise characterizing the model using one or more aspects of the biological state of one or more cellular constituents in the plurality of cellular constituents. The memory further stores instructions for repeating the instructions for computing one or more times, thereby computing the plurality of models. The memory also stores instructions for communicating each model characterization computed in an instance of the instructions for computing. In some embodiments, the instructions for receiving data comprise instructions for receiving the data from a remote computer over a wide area network, such as the Internet. In some embodiments, the biological sample class is a disease such as cancer.

Another aspect of the invention provides a computer comprising a central processing unit and a memory, coupled to the central processing unit. The memory stores instructions for receiving data. The data comprises one or more aspects of the biological state of each cellular constituent in a plurality of cellular constituents that have been measured in a test organism of a species or a test biological specimen from an organism of the species. The memory further stores instructions for computing a plurality of models. This computing produces a model characterization for each model in the plurality of models that indicates whether the test organism of the species or the test biological specimen from the organism of the species is a member of a biological sample class. The computing comprises characterizing each model in the plurality of models using one or more aspects of the biological state of one or more cellular constituents in the plurality of cellular constituents. The memory further stores instructions for communicating each model characterization computed by the instructions for computing.

Still another aspect of the invention provides a computer program product for use in conjunction with a computer system. The computer program product comprises a computer readable storage medium and a computer program mechanism embedded therein. The computer program mechanism further comprises instructions for receiving data. Such data comprises one or more aspects of the biological state of each cellular constituent in a plurality of cellular constituents that have been measured in a test organism of a species or a test biological specimen from an organism of the species. The computer program mechanism further comprises instructions for computing a model in a plurality of models. Such computing produces a model characterization for the model that indicates whether the test organism of the species or the test biological specimen from the organism of the species is a member of a biological sample class. The computation of the model comprises characterizing the model using one or more aspects of the biological state of one or more cellular constituents in the plurality of cellular constituents. The computer program mechanism further comprises instructions for repeating the instructions for computing one or more times, thereby computing the plurality of models. The computer program mechanism also comprises instructions for communicating each model characterization computed in an instance of the instructions for computing.

Still another aspect of the invention comprises a computer program product for use in conjunction with a computer system. The computer program product comprises a computer readable storage medium and a computer program mechanism embedded therein. The computer program mechanism comprises instructions for receiving data. The data comprises one or more aspects of the biological state of each cellular constituent in a plurality of cellular constituents that have been measured in a test organism of a species or a test biological specimen from an organism of the species. The computer program mechanism further comprises instructions for computing a plurality of models. The computing produces a model characterization for each model in the plurality of models that indicates whether the test organism of the species or the test biological specimen from the organism of the species is a member of a biological sample class. The computing comprises characterizing each model in the plurality of models using one or more aspects of the biological state of one or more cellular constituents in the plurality of cellular constituents. The computer program mechanism further comprises instructions for communicating each model characterization computed by the instructions for computing.

Another aspect of the invention provides a method that comprises receiving data. Such data comprises one or more aspects of the biological state of each cellular constituent in a plurality of cellular constituents that have been measured in a test organism of a species or a test biological specimen from an organism of the species. A model in a plurality of models is computed. The computing produces a model characterization for the model that indicates whether the test organism of the species or the test biological specimen from the organism of the species is a member of a biological sample class. The computing of the model comprises characterizing the model using one or more aspects of the biological state of one or more cellular constituents in the plurality of cellular constituents. The computing is repeated one or more times thereby computing the plurality of models. Each of the model characterization computed in an instance of the computing is then communicated.

Still another aspect of the invention comprises receiving data. The data comprises one or more aspects of the biological state of each cellular constituent in a plurality of cellular constituents that have been measured in a test organism of a species or a test biological specimen from an organism of the species. A plurality of models is computed. Such computing produces a model characterization for each model in the plurality of models that indicates whether the test organism of the species or the test biological specimen from the organism of the species is a member of a biological sample class. The computing comprises characterizing each model in the plurality of models using one or more aspects of the biological state of one or more cellular constituents in the plurality of cellular constituents. Each computed model characterization communicated.

4. BRIEF DESCRIPTION OF THE DRAWINGS

Like reference numerals refer to corresponding parts throughout the several views of the drawings.

5. DETAILED DESCRIPTION

Figure 1:
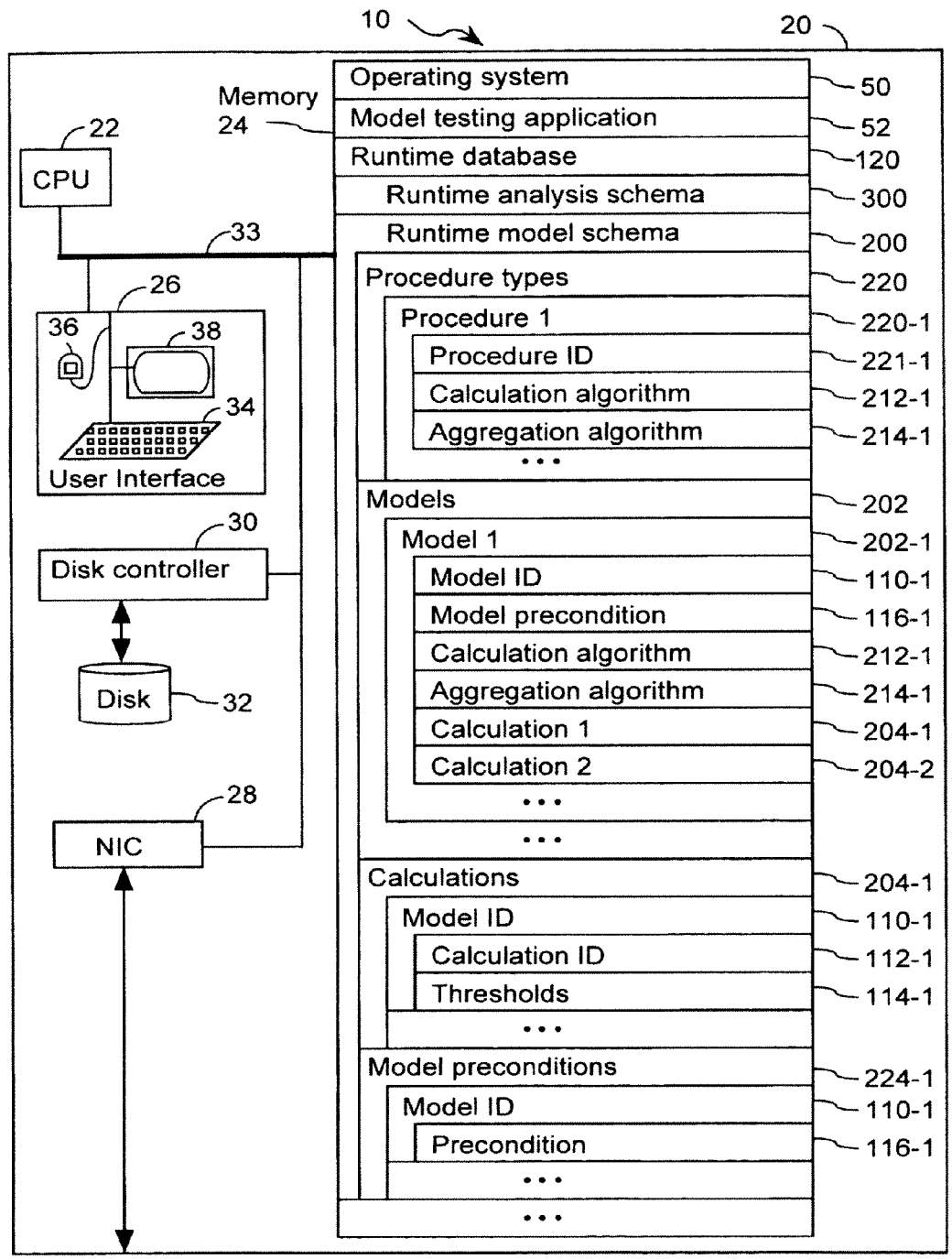
FIG. 1 illustrates a computer system for classifying a biological specimen in accordance with one embodiment of the present invention.
Figure 2:
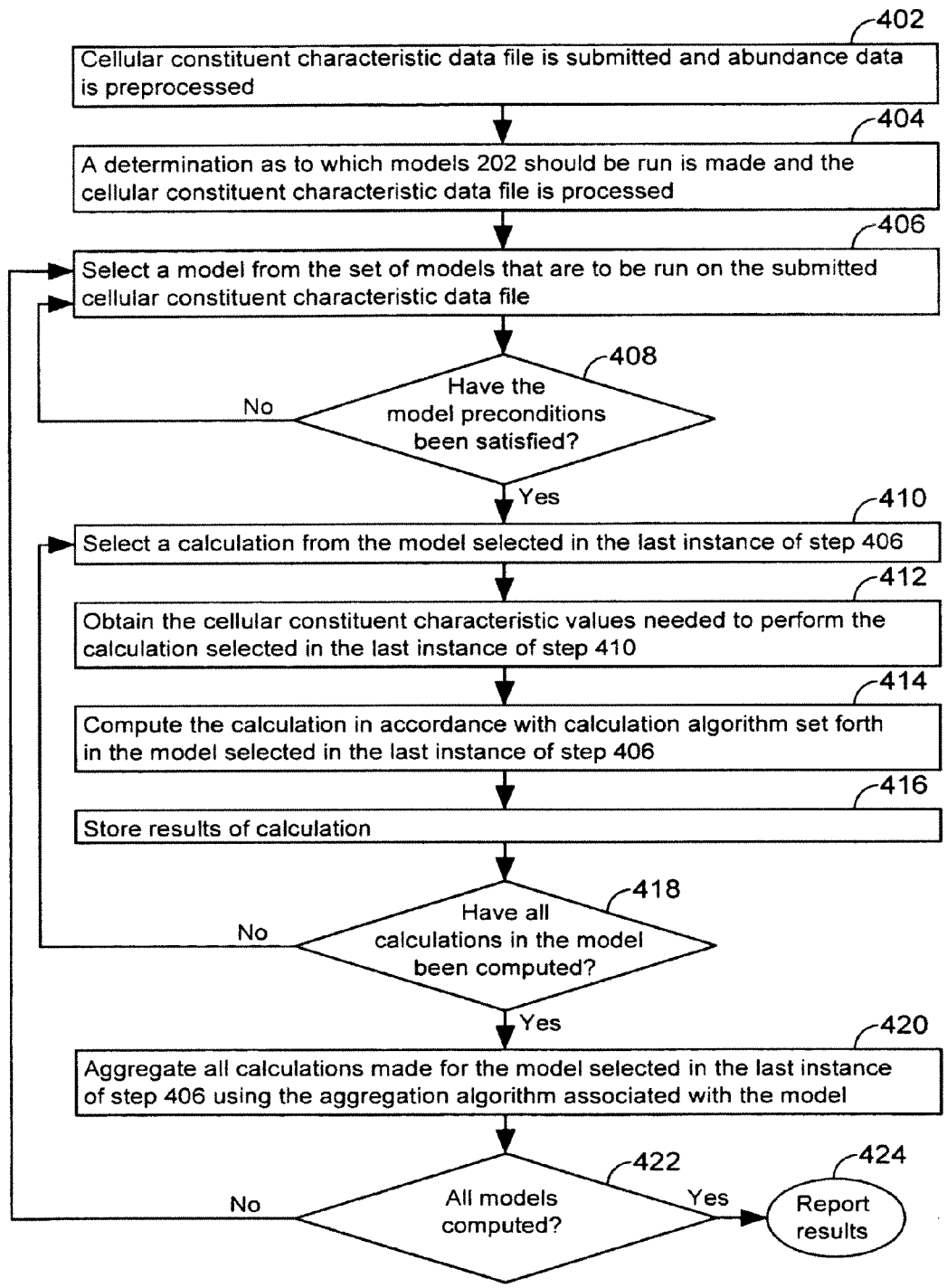
FIG. 2 illustrates processing steps for using a plurality of classifiers to classify a specimen in accordance with one embodiment of the present invention.
Figure 3:
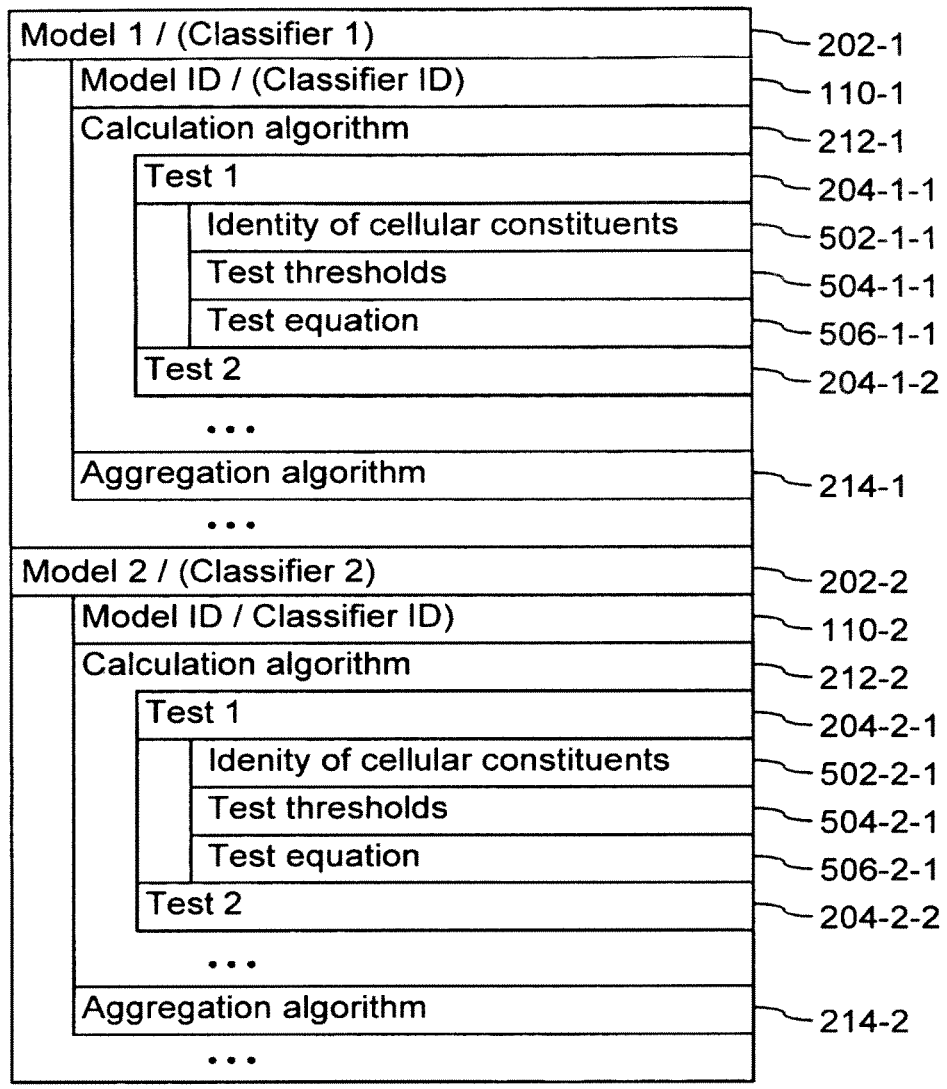
FIG. 3 illustrates a data structure that stores a plurality of models (classifiers) in accordance with one embodiment of the present invention.

FIG. 1 illustrates a system 10 that is operated in accordance with one embodiment of the present invention. FIG. 3 illustrate data structures that are useful for storing data used in the present invention. FIG. 2 illustrates processing steps used to test a plurality of models in accordance with one embodiment of the present invention. Using the processing steps outlined in FIG. 2, such models are capable of determining whether a specimen has one or more biological features. These figures will be referenced in this section in order to disclose the advantages and features of the present invention. Representative biological features are disclosed in Section 5.4, below.

System 10 comprises at least one computer 20 (FIG. 1). Computer 20 comprises standard components including a central processing unit 22, memory 24 for storing program modules and data structures, user input/output device 26, a network interface card 28 for coupling computer 20 to other computers in system 10 or other computers via a communication network (not shown), and one or more busses 33 that interconnect these components. User input/output device 26 comprises one or more user input/output components such as a mouse 36, display 38, and keyboard 34. Computer 20 further comprises a disk 32 controlled by disk controller 30. Together, memory 24 and disk 32 store program modules and data structures that are used in the present invention.

Memory 24 comprises a number of modules and data structures that are used in accordance with the present invention. It will be appreciated that, at any one time during operation of the system, a portion of the modules and/or data structures stored in memory 24 is stored in random access memory while another portion of the modules and/or data structures is stored in non-volatile storage 32. In a typical embodiment, memory 24 comprises an operating system 50. Operating system 50 comprises procedures for handling various basic system services and for performing hardware dependent tasks. Memory 24 further comprises a file system (not shown) for file management. In some embodiments, this file system is a component of operating system 50.

Now that an overview of an exemplary computer system in accordance with the present invention has been detailed, an overview of exemplary data structures used in accordance with one embodiment of the present invention is presented below in Section 5.1. Then, in Section 5.2, detailed processing steps for testing a plurality of models using such exemplary data structures are described. In Section 5.3, examples of the results provides by the present invention are provided.

5.1. Exemplary Data Structures

Exemplary data structures used in one embodiment of the present invention are illustrated in FIG. 1. A model testing application 52 uses runtime database 120. Runtime database 120 is modeled such that it includes a runtime analysis schema 300 and a runtime model schema 200. These schemas describe the organization of a number of different types of tables in runtime database 120. In preferred embodiments, database 120 is any form of data storage apparatus, including but not limited to a flat file, a relational database (SQL), and an OLAP database (MDX and/or variants thereof). In some specific embodiments, database 120 is a hierarchical OLAP cube. In some specific embodiments, database 120 comprises a star schema that is not stored as a cube but has dimension tables that define hierarchy. Still further, in some embodiments, database 120 has hierarchy that is not explicitly broken out in the underlying database or database schema (e.g., dimension tables are not hierarchically arranged). In some embodiments, database 120 is a database in a format such as Oracle, MS Access 95/97/2000 or better, Informix, Sybase, Interbase, IBM DB2, Paradox, dBase, SQL Anywhere, Ingres, MsSQL, MS SQL server, ANSI Level 2, or PostgreSQL. In some embodiments, runtime database 120 includes a runtime model schema 200 and a runtime analysis schema 300.

A fundamental table type specified by runtime model schema 200 is a model 202. The goal of a model 202 is to attempt to determine the likelihood that a biological specimen (e.g., a tumor) has a biological feature (e.g., breast cancer, lung cancer, etc.). As such, each model 202 is associated with a biological feature. As used herein, biological features are any distinguishable phenotype exhibited by one or more biological specimens. For example, in one application of the present invention, each biological feature refers to an origin or primary tumor type. It has been estimated that approximately four percent of all patients diagnosed with cancer have metastatic tumors for which the origin of the primary tumor has not been determined. See, for example, Hillen, 200, Postgrad. Med. J. 76, p. 690. On occasion, the primary site for a metastatic tumor is not clearly apparent even after pathological analysis. Thus, predicting the primary tumor site of origin for some of these cancers represent an important clinical objective. In the case of tumor of unknown primary origin, representative biological sample classes include carcinomas of the prostate, breast, colorectum, lung (adenocarcinoma and squamous cell carcinoma), liver, gastroesophagus, pancreas, ovary, kidney, and bladder/ureter, which collectively account for approximately seventy percent of all cancer-related deaths in the United States. See, for example, Greenlee et al., 2001, CA Cancer J. Clin. 51, p. 15. Section 5.4, below, describes additional examples of biological sample classes in accordance with the present invention.

To illustrate how a model 202 can be used to determine the likelihood of whether a biological specimen is a member of a biological sample class, consider the case in which a particular model 202 represents the likelihood that a biological sample has lung cancer. Further hypothesize that this lung cancer model is applied to a biological specimen and the result of the test indicates that there is a high likelihood that the biological specimen has lung cancer. In some embodiments, each respective model 202 in runtime database 120 includes a model identifier 110 that uniquely identifies the respective model. In addition, each model 202 specifies one or more calculations 204 (also termed tests). In some embodiments, a model 202 specifies between two and one thousand calculations. In more preferred embodiments, each model 202 specifies between three calculations and five hundred calculations, between three calculations and one hundred calculations, or between three calculations and fifty calculations.

Each calculation 204 in a model 202 specifies the identity of certain cellular constituents. For example, in one instance, each respective calculation 204 specifies a first cellular constituent and a second cellular constituent. To illustrate, consider the case in which there are four calculations 204 in a model 202 as described in Table 1:

TABLE 1

Exemplary calculations 204

| Calculation number | First cellular constituent | Second cellular constituent |
|---|---|---|
| 1 | Gene AAA | Gene DDD |
| 2 | Gene CCC | Gene DDD |
| 3 | Gene NNN | Gene MMM |
| 4 | Gene XXX | Gene YYY |

Thus, calculation 1 specifies a first cellular constituent AAA and a second cellular constituent DDD, and so forth.

In addition to specifying calculations 204, each model 202 specifies a calculation algorithm 212 that is to be used to apply each calculation 204 in the model. A calculation algorithm 212 specifies the operational relationship between cellular constituent abundance values when a calculation 204 in a model 202 is computed. The cellular constituent abundance values are taken from a biological specimen that is to be classified by a model 202.

One instance of a calculation algorithm 212 is a ratio, where the ratio numerator is determined by an abundance of a first cellular constituent in a biological specimen and the ratio denominator is determined by an abundance of a second cellular constituent in the biological specimen. In this instance, the calculation algorithm 212 specifies that a ratio between the two cellular constituent abundance values is to be taken whereas the calculation 204 specifies the actual identity of the cellular constituents in the test biological specimen that are to be used when computing the calculation 204 in accordance with the calculation algorithm 212. For example, one calculation algorithm 212 specifies to take the ratio of an abundance of a first cellular constituent, as the numerator, to the abundance of a second cellular constituent, as the denominator. This calculation algorithm 212 is used in each calculation 204 in an exemplary model 202. In the case of calculation number 1 of Table 1, an exemplary calculation algorithm 212 specifies to take the ratio between gene AAA and gene DDD, in the case of calculation number 2, the calculation algorithm 212 specifies to take the ratio between gene CCC and gene DDD, and so forth.

The present invention encompasses a wide range of calculation algorithms 212 in addition to ratios between a first cellular constituent and a second cellular constituent. For example, in some embodiments, a calculation algorithm 212 can specify that the abundance value for a first cellular constituent be multiplied by the abundance value for a second cellular constituent (A×B). In fact, calculation algorithm 212 can specify that the product of the abundance values of the first two cellular constituents be multiplied by the abundance value of a third cellular constituent (A×B×C). Alternatively, calculation algorithm 212 can specify that the product of the abundance values of the first two cellular constituents be divided by the abundance value of a third cellular constituent [(A×B)/C)]. As these examples illustrate, a calculation algorithm is any mathematical operation, or set of mathematical operations (e.g., multiplication, division, logarithm, etc.) of any combination of cellular constituents. A calculation algorithm 212 does not indicate the actual identity of the cellular constituents that are to be used to compute any given calculation 204. A calculation 204, on the other hand, specifies a set of cellular constituents but does not indicate the operational relationship between the cellular constituents that is used to compute the calculation 204. By applying a calculation algorithm 212 to a calculation 204, the calculation 204 can be computed in accordance with the methods of the present invention.

In some embodiments, each respective calculation 204 includes a model identifier 110 that specifies the model 202 to which the calculation belongs. Further, each calculation includes thresholds 114. For example, in some embodiments, each calculation 204 includes a lower threshold and an upper threshold. In such embodiments, each calculation 204 in a model 202 is computed by applying the calculation algorithm 212 for the model 202 to the calculations as described above. When the computed calculation 204 is below the lower threshold the calculation is characterized as negative. When the computed calculation 204 is above the upper threshold the calculation is characterized as positive. When the computed calculation 204 is between the lower threshold and the upper threshold, the calculation is characterized as indeterminate. For more information on how such thresholds can be computed, as well as more detailed examples of models and their uses in accordance with the present invention, see copending U.S. Patent Application Ser. No. 60/507,381 entitled "Systems and Methods for Analyzing Gene Expression Data For Clinical Diagnostics" to Anderson, as well as U.S. patent application Ser. No. to be determined, entitled "Systems and Methods for Analyzing Gene Expression Data for Clinical Diagnostics," to Moraleda and Anderson, filed Jun. 4, 2004.

To illustrate a calculation (test) where upper and lower thresholds are used, consider the case of calculation 1 from Table 1, where the abundance of gene AAA ([AAA]) is 1000 and the abundance of DDD ([DDD]) is 100 in a biological specimen. Further, calculation 1 specifies a lower threshold of 0.8 and an upper threshold is 5. The calculation algorithm 212 for the model 202 that includes calculation 1 indicates that a ratio between the first gene and second gene is to be taken. When this calculation algorithm 212 is applied to calculation 204, the computed calculation, ratio [AAA]/[DDD], has the value 10 (1000/100). Because the ratio is greater than the upper ratio threshold, the calculation 204 is characterized as "positive."

In another example, [AAA] has a value of 70 in a biological specimen and [DDD] has a value of 100 in the biological specimen. Further, calculation 1 specifies a lower threshold of 0.8 and an upper threshold of 5. In such an instance, the ratio [AAA]/[DDD] has the value 0.7 (70/100). Because the ratio is less than the lower threshold, the calculation is characterized as "negative."

In still another example, [AAA] has a value of 120 in a biological specimen and [DDD] has a value of 100 in the biological specimen. Further, calculation 1 specifies a lower threshold of 0.8 and an upper threshold of 5. In such an instance, the ratio [AAA]/[DDD] has the value 1.2 (120/100). Because the ratio is greater than the lower threshold but less than the upper threshold, the calculation is characterized as "indeterminate."

In addition to a calculation algorithm 212, each model 202 includes an aggregation algorithm 214 that specifies how the calculations 204 for a given model 202 are to be combined in order to characterize (compute) the model. One example of an aggregation algorithm 214 is a voting scheme where the model 202 is characterized as having a high probability or likelihood if more of the calculations in the model are positive, when computed, then are negative. For example, consider the case in which a calculation algorithm 212 is applied to the calculations of Table 1, above, and that calculations 1 and 2 are positive, calculation 3 is indeterminate, and calculation 4 is negative. When this is the result, an organism that is tested using the model that consists of the calculations in Table 1 will be characterized as having a likelihood of having the biological feature associated with the model.

Each model 202 optionally includes model preconditions 116. A model precondition 116 specifies a requirement that is to be satisfied before a calculation algorithm 212 is applied to the calculations 204 of the model. An example of a model precondition 116 is the requirement that the calculations 204 of another predetermined model 202 be computed before the calculations 204 of the model 202 associated with the precondition 116 are computed. For example, consider the case in which there is a model 202 for lung cancer and another model 202 for lung adenocarcinoma. The model for lung cancer is used to determine whether a particular tumor is positive for lung cancer. In this case, the model 202 for lung adenocarcinoma can have a precondition 116 that requires that the model for lung cancer be run before the model for lung adenocarcinoma is run. The precondition 116 can further require that the model for lung cancer test positive before the model for lung adenocarcinoma is run.

In addition to the model 202 table type, runtime model schema 200 specifies other tables in a hierarchical manner. At the top of this hierarchy are procedure types 220. Each procedure type 220 specifies a calculation algorithm 212 and an aggregation algorithm 214. Furthermore, each procedure type 220 optionally includes a procedure identifier 221.

One or more models 202 can be associated with a procedure type 220. When a model 202 is associated with a procedure type 220, the model uses the calculation algorithm 212 and aggregation algorithm 214 specified by the procedure type 220. In one example, a model 202 includes the procedure identifier 221 of a procedure 220 that is to be used by the model. In such an example, the model 202 need not include explicit information about the calculation algorithm 212 and the aggregation algorithm 214 to be used by the model because such information can be obtained from the procedure 220 designated by the procedure identifier field 221 in the model 202.

As illustrated in FIG. 1 and discussed above, each model 202 includes one or more calculations 204. In fact, in some embodiments, each calculation 204 is stored in another form of table that is found in runtime model schema 200. Each calculation 204 specifies one or more cellular constituent abundance values (not shown). In addition, each calculation 204 can optionally include a model identifier 110 that identifies the model 202 to which the calculation 204 is associated. For example, the model identifier 110 can indicate that the calculation 204-1 is associated with model 202-1. Further, each calculation 204 can have a calculation identifier 112 and thresholds 114. In the case where each calculation 204 includes a model identifier 110, models 202 of runtime database 120 need not explicitly describe the calculations 204 that are part of such models. If the calculations 204 for a given model 202 are desired, they can be identified by searching through the calculations 204 in runtime database 120 for calculations that have a model identifier 110 that matches the given model.

As illustrated in FIG. 1 and discussed above, each model 202 includes one or more model preconditions 224. In fact, each model precondition 224 is another form of data structure that is found in runtime model schema 200. Each precondition 224 specifies a precondition 116 that is satisfied before the model associated with the precondition is run. In addition, each model precondition 224 can optionally include a model identifier 110 that identifies the model 202 to which the precondition is associated. For example, a model identifier 110 can indicate that a precondition 224-1 is associated with a model 202-1. In the case where each precondition 224 includes a model identifier 110, models 202 of runtime database 120 need not explicitly describe the preconditions 224 that are part of such models. In such instances, to determine which preconditions 224 apply to a given model 202, a search through the preconditions in runtime database 120 for preconditions that have a model identifier 110 that matches the given model is made.

5.2. Exemplary Processing Steps

Exemplary data structures in accordance with one embodiment of the present invention were introduced in Section 5.1. This section describes how such novel data structures can be used to test a plurality of models 202. In Section 5.3, results of such calculations will be described.

Step 402.

In step 402 cellular constituent characteristic data is obtained. Typically, the cellular constituent characteristic data is in the form of a cellular constituent abundance data file that is submitted by a clinician at a remote site. In some instances, when the data file is submitted, computer 20 receives the file via network interface card 28. In typical embodiments a remote computer transmits the data to computer 20 over a wide area network (WAN) such as the Internet.

The cellular constituent characteristic data file typically includes aspects (also termed characteristics) of the biological state of each cellular constituent in a plurality of cellular constituents. For instance, in some embodiments, the cellular constituent characteristic file comprises abundance data for several cellular constituents in a given biological specimen or organism. The cellular constituent abundance data file can include data for more than one hundred cellular constituents in a given biological specimen. In fact, the cellular constituent abundance data file can include data for more than 500, more than 1000, more than 10,000, or more than 15,000 cellular constituents in a given biological specimen. In some embodiments, a cellular constituent abundance data file includes data for multiple biological specimens. In such embodiments, the data file clearly indicates which biological specimen is associated with each cellular constituent abundance level that is in the file.

In some embodiments, the cellular constituent characteristic data file is in a format designed for AFFYMETRIX (Santa Clara, Calif.) GeneChip probe arrays (e.g. AFFYMETRIX chip files with a CHP extension that are generated using AFFYMETRIX MAS4.0 software and U95A or U133 gene chips), a format designed for AGILENT (Palo Alto, Calif.) DNA microarrays, a format designed for AMERSHAM (Little Chalfont, England) CodeLink microarrays, the ARRAYVISION file format by Imaging Research (St. Catharines, Canada), the AXON (Union City, Calif.) GenePix file format, the BIODISCOVERY (Marina del Rey, Calif.) IMAGENE file format, the ROSETTA (Kirkland, Wash.) gene expression markup language (GEML) file format, a format designed for INCYTE (Palo Alto, Calif.) GEM microarrays, or a format developed for MOLECULAR DYNAMICS (Sunnyvale, Calif.) cDNA microarrays.

In some embodiments, the cellular constituent characteristic file comprises a processed microarray image for a biological specimen. For example, in one such embodiment, the file comprises cellular constituent abundance information for each cellular constituent represented on the array, optional background signal information, and optional associated annotation information describing the probe used for the respective cellular constituent. In some embodiments, cellular constituent abundance measurements are transcriptional state measurements as described in Section 5.5, below.

In some embodiments of the present invention, aspects (characteristics) of the biological state, other than the transcriptional state, such as the translational state, the activity state, or mixed aspects of the biological state, are represented in a cellular constituent characteristic file. See, for example, Section 5.6, below. For instance, in some embodiments, the cellular constituent characteristic file includes protein levels for various proteins in a biological specimen under study. In some specific embodiments, the cellular constituent characteristic file comprises amounts or concentrations of cellular constituents in tissues of a biological specimen under study, cellular constituent activity levels in one or more tissues of the biological specimen, or the state of modification (e.g., phosphorylation) of one or more cellular constituents of the biological specimen.

In one aspect of the present invention, the expression level of a gene in a biological specimen is determined by measuring an amount of at least one cellular constituent that corresponds to the gene in one or more cells of a biological specimen under study. In one embodiment, the amount of at least one cellular constituent that is measured comprises abundances of at least one RNA species present in one or more cells of the biological specimen. Such abundances can be measured by a method comprising contacting a gene transcript array with RNA from one or more cells of the organism, or with cDNA derived therefrom. A gene transcript array comprises a surface with attached nucleic acids or nucleic acid mimics. The nucleic acids or nucleic acid mimics are capable of hybridizing with the RNA species or with cDNA derived from the RNA species. In one particular embodiment, the abundance of the RNA is measured by contacting a gene transcript array with the RNA from one or more cells of an organism under study, or with nucleic acid derived from the RNA, such that the gene transcript array comprises a positionally addressable surface with attached nucleic acids or nucleic acid mimics, wherein the nucleic acids or nucleic acid mimics are capable of hybridizing with the RNA species, or with nucleic acid derived from the RNA species.

In some embodiments, the cellular constituent characteristic file comprises gene expression data for a plurality of genes (or cellular constituents that correspond to the plurality of genes). In one embodiment, the plurality of genes comprises at least five genes. In another embodiment, the plurality of genes comprises at least one hundred genes, at least one thousand genes, at least twenty thousand genes, or more than thirty thousand genes. In some embodiments, the plurality of genes comprises between five thousand and twenty thousand genes.

In some implementations of step 402, the abundance data is preprocessed. In some embodiments, this preprocessing involves a standardization in which all the cellular constituent characteristic values for a given biological specimen are divided by the median cellular constituent abundance value measured for the biological specimen. In some embodiments, all the cellular constituent abundance values for a given biological specimen or organism are divided by an average of the $25^{th}$ and $75^{th}$ percentile of the cellular constituent abundance values measured for the biological specimen.

In the case where the source of the cellular constituent abundance measurements is a microarray, negative cellular constituent abundance values can be obtained when a mismatched probe measure is greater than a perfect match probe. This typically occurs when the primary gene (representing a cellular constituent) is expressed at low levels. In some representative cases, on the order of thirty percent of the abundance values in a given cellular constituent abundance file are negative. In some instances of the preprocessing of the present invention, all cellular constituent abundance values with a value of zero or less are replaced with a fixed value. In the case where the source of the cellular constituent abundance measurements is an AFFYMETRIX GENECHIP MAS 5.0, negative cellular constituent abundance values can be replaced with a fixed value, such as 20 or 100, in some embodiments. More generally, in some embodiments, all cellular constituent abundance values with a value of zero or less are replaced with a fixed value that is between 0.001 and 0.5 (e.g., 0.1 or 0.01) of the median cellular constituent abundance value for a given biological specimen. In some embodiments, all cellular constituent abundance values are replaced with a transformation of the value that varies between the median and zero inversely in proportion to the absolute value of the cellular constituent abundance value that is being replaced. In some embodiments, all cellular constituent abundance values with a value less than zero are replaced with a value that is determined based on a function of the magnitude of their initial negative value. In some instances, this function is a sigmoidal function.

In some embodiments, step 402 is facilitated by a web page that is either on computer 20 or that is addressable by computer 20. The web page allows a remote user to select which models are to be run and facilitates the transfer of the cellular constituent data file from the remote site to computer 20. In some embodiments, the web page allows for the transfer of any of the following information:

an address of the lab requesting computation of one or models;

an identity of the one or models (suites) that should be run using the cellular constituent characteristic data file;

a unique specimen identifier that identifies the specimen submitted;

an identifier that identifies the microarray format used to measure cellular constituent characteristic data;

an identifier that identifies the patient represented by the cellular constituent characteristic data file;

a description of the biological specimen from which cellular constituent characteristic data was obtained for the cellular constituent characteristic file; and/or an identity of a physician or other health care professional that ordered the models to be run on the biological specimen.

In some embodiments, rather than, or in addition to, using a web-page based interface, a software module (not shown) is run on the remote originating computer. The software module allows the remote clinician to upload the requisite data to computer 20 using file transfer protocol, interne protocol, or other types of file sharing techniques. In some embodiments, all communication between computer 20 in step 402 (and in step 424) is encrypted using encryption algorithms known in the art such as secret key cryptography, hashes, message digests, and/or public key algorithms. Such techniques are enclosed in, for example, Kaufman, *Network Security*, 1995, Prentice-Hall, New Jersey; and Schneier, *Applied Cryptography Protocols, Algorithms, and Source Code in C*, Second Edition, John-Wiley & Sons, Inc., each of which is hereby incorporated by reference in its entirety.

Steps 404 and 406.

In step 404 a determination is made as to which models 202 should be run (computed). For example, in some cases, models 202 in runtime database 120 are divided into suites of models. In one example, there is a suite of models to test for cancer of unknown primary, another suite of models specifically designed to test for lung cancer, and so forth. Each suite of models 202 includes one or more models. Thus, in some instances, step 404 involves determining which suite of models 202 was requested by a user. In step 406, a model from the set of models selected in step 404 is selected.

Step 408.

Step 408 is optional. In some embodiments, step 408 is not run and all the models specified by the remote user in step 402 (e.g., all models in a selected suite) are run. In optional step 408, a determination is made as to whether the model preconditions 116 have been satisfied for the model 202 selected in step 406. For example, in some embodiments, a model precondition 116 can specify that a model 202 that is indicative of a broader biological sample class (e.g., a more general phenotype) than the model selected in the last instance of step 406 must be run before a certain model 202, indicative of a narrower biological sample class, is run. To illustrate, a model precondition 116 of a first model 202 that is indicative of a particular form of lung cancer could require that a second model 202, that is indicative of lung cancer generally, test positive prior to running the first model. Further, the second model 202 could have a model precondition 116 that requires that a third model, which is indicative of cancer, test positive prior to running the second model. In some embodiments, a model precondition 116 comprises a requirement that another model in a plurality of models be identified as negative, positive, or indeterminate prior to testing the selected model. A few additional examples of how preconditions 116 can be used to arrange models 202 into hierarchies follow.

In a first example, the preconditions of model B require that model A have a specific result before model B is run. It may well be the case that model A is run, yet fails to yield the specific result required by model B. In this case, model B is never run. If, however, model A is run and yields the specific result required by model B, then model B is run. This example can be denoted as:

if (A=result), then B can be run.

In a second example, the preconditions 116 of model C require that either model A has a specific result or that model B has a specific result prior to running model C. This example can be denoted as:

if ((A=first result) or (B=second result)), then C can be run. To illustrate, a model C can require that model A be run and test positive for cancer or that model B be run and test positive for lung cancer, before model C is run. Alternatively, the preconditions 116 of model C could require that both model A and model B achieve specific results:

if ((A=first result) and (B=second result)), then C can be run.

In a another example, the preconditions 116 of model D require that model C has a specific result before model D is run. The preconditions 116 of model C, in turn, require that model A has a first result and that model B has a second result before model C is run. This example can be denoted as:

If ((A=first result) and (B=second result)), then C can be run

If (C=third result), then D can be run.

These examples illustrate the advantages that model preconditions 116 provide. Because of the novel preconditions 116 of the present invention, models 202 can be arranged into hierarchies in which specific models 202 are run before other models 202 are run. Often, the models 202 run first are designed to classify a biological specimen into a broad biological sample class (e.g., broad phenotype). Once the biological sample has been broadly classified, subsequent models 202 are run to refine the preliminary classification into a narrower biological sample class (e.g., a more specific biological sample class).

When the model preconditions 116 for a model 202 selected in step 406 have been satisfied (408—Yes), process control passes to step 410. When the model preconditions 116 for the model 202 have not been satisfied (408—No), process control passes back to step 406 where another model 202 from the set models identified in step 404 is selected.

Step 410.

A calculation 204 in the model is selected in step 410. A calculation 204 identifies two or more cellular constituents whose characteristics (aspects of the biological state of the cellular constituent) are to be tested in the biological specimen under study. For example, a calculation 204 can specify cellular constituent abundance values for genes AAA and BBB. In some embodiments, a calculation specifies at least one cellular constituent that is up-regulated or down-regulated in specimens that have the biological feature represented by the model 202 selected in the last instance of step 406 relative to biological specimens that do not have the biological feature represented by model 202 and/or have a different biological feature.

Cellular constituents that are up-regulated or down-regulated in specimens having certain biological features relative to specimens having other biological features can be obtained through routine experimentation or in published references. For example, Su et al. 2001, Cancer Research 61, p. 7388 provides the names of genes that are both (i) up-regulated in specific primary tumor types and (ii) predictive of such tumor types. Su et al. identified the expression of the cellular constituents listed in Table 2 with prostate tumors.

TABLE 2

Su et al. Cellular constituents that are up-regulated in prostate tumors.

| Number | Accession Name | Name | Description |
|---|---|---|---|
| 1 | NM_003656 | CAMK1 | calcium/calmodulin-dependent protein kinase I |
| 2 | Hs.12784 | KIAA0293 | KIAA0293 protein |
| 3 | NM_001648 | KLK3 | kallikrein 3, (prostate specific antigen) |
| 4 | NM_005551 | KLK2 | kallikrein 2, prostatic |
| 5 | None | TRG@ | T cell receptor gamma locus transcription factor similar to *D. melanogaster* homeodomain protein |
| 6 | NM_006562 | LBX1 | lady bird late |
| 7 | NM_016026 | LOC51109 | CGI-82 protein |
| 8 | NM_001099 | ACPP | acid phosphatase, prostate |
| 9 | NM_005551 | KLK2 | kallikrein 2, prostatic |
| 10 | None | none | Antigen|TIGR == HG2261-HT2352 |
| 11 | NM_012449 | STEAP | six transmembrane epithelial antigen of the prostate |
| 12 | NM_001099 | ACPP | acid phosphatase, prostate |
| 13 | NM_004522 | KIF5C | kinesin family member 5C |
| 14 | None | none | Antigen|TIGR == HG2261-HT2351 |
| 15 | NM_001634 | AMD1 | S-adenosylmethionine decarboxylase 1 |
| 16 | NM_001634 | AMD1 | S-adenosylmethionine decarboxylase 1 |
| 17 | None | none | Antigen|TIGR == HG2261-HT2351 |
| 18 | NM_006457 | LIM | LIM protein (similar to rat protein kinase C-binding enigma) |
| 19 | NM_001648 | KLK3 | Kallikrein 3, (prostate specific antigen) |

In some embodiments, a cellular constituent is deemed to be up-regulated in specimens having a biological feature when the abundance of the cellular constituent in biological specimens having the biological feature is greater than the abundance of at least sixty percent, at least seventy percent, at least eighty percent or at least ninety percent of the cellular constituents in biological specimens having the biological feature for which a plurality of cellular constituent abundance measurements have been made. In some embodiments, a cellular constituent is deemed to be up-regulated in specimens having a biological feature relative to biological specimens that do not have the biological feature when the abundance of the cellular constituent in biological specimens having the biological feature is, on average, higher than the abundance of the cellular constituent in biological specimens that do not have the biological feature. In some embodiments, a cellular constituent is deemed to be down-regulated in specimens having a biological feature when the abundance of the cellular constituent in biological specimens having the biological feature is less than the abundance of at least forty percent, at least thirty percent, at least twenty percent, or at least ten percent of the cellular constituents in biological specimens having the biological feature for which a plurality of cellular constituent abundance measurements have been made. In some embodiments, a cellular constituent is deemed to be down-regulated in biological samples or organisms relative to biological samples or organisms that do not have the biological feature when the abundance of the cellular constituent in biological specimens that have the biological feature is, on average, less than the abundance of the cellular constituent in biological specimens that do not have the biological feature.

In some embodiments, the cellular constituents specified in a calculation 204 are each a nucleic acid or a ribonucleic acid and the abundance of these cellular constituents in a biological specimen is obtained by measuring a transcriptional state of all or a portion of the first cellular constituent and the second cellular constituent in the biological specimen. In some embodiments, the cellular constituents specified by a calculation 204 are each independently all or a fragment of an mRNA, a cRNA or a cDNA. In some embodiments, the cellular constituents specified by a calculation 204 are each proteins and the abundance of these cellular constituents is obtained by measuring a translational state of all or a portion of the cellular constituents. In some embodiments, the abundance of the cellular constituents specified by a calculation 204 is determined by measuring an activity or a post-translational modification of the cellular constituents.

Step 412.

In step 412, the cellular constituent characteristic values specified in the calculation 204 selected in the last instance of step 410 are obtained from the cellular constituent characteristic submitted in step 402. Thus, in the example where calculation 204 specifies gene AAA and gene BBB, the cellular constituent abundance values (or some other characteristic specified by the calculation) for gene AAA and gene BBB are obtained from the cellular constituent abundance file.

Step 414.

In step 414, the calculation 204 selected in the last instance of step 410 is computed in accordance with the calculation algorithm 212 specified in the model. For example, the calculation algorithm can specify to take the ratio between the abundance values of the first cellular constituent specified in an exemplary calculation 204 and the second cellular constituent specified in an exemplary calculation 204. Additional examples of computing calculations 204 in accordance with a calculation algorithm 214 have been described in Section 5.1, above. These examples describe how a calculation 204 can be characterized after it has been computed based on the value of the computed calculation relative to threshold values for the calculation. For example, if the computed calculation 204 has a value that is greater than the true minimum for the calculation, then the computed calculation 204 is characterized as positive.

Step 416.

In step 416, results of the computation of the last calculation 204 are stored. In some embodiments, storage includes the storage of a model identifier that identifies the model 202 for which the calculation 204 was run, a model version identifier that indicates which version of the model 202 was run, an expression datafile identifier that identifies the cellular constituent characteristic data file that supplied the cellular constituent characteristic values used to compute the calculation 204, the calculation identifier 112 (FIG. 1) associated with the calculation 204, and the calculation result code (e.g., "extremely likely", "not likely", etc.).

Step 418.

In step 418 a determination is made as to whether all the calculations 204 in the model 202 have been computed in accordance with the calculation algorithm 212 for the model. If not (418—No), process control returns to step 410 where another calculation (test) 202 is selected from the model 202 for computation. If so (418—Yes), network control passes to step 420.

Step 420.

In step 420, all calculations (tests) 204 that have been made for the model selected in the last instance of step 406 are aggregated in accordance with the aggregation algorithm 214 specified by the model 202. Such aggregation results in a model characterization for the model. This model characterization indicates whether the test organism of the species or the test biological specimen from the organism of the species is a member of a biological sample class.

In one embodiment, the result code of each row in table 318 with a model identifier matching the model identifier for the model 202 selected in the last instance of step 406 is collected. For example, consider the case in which a model 202 includes five calculations 204. Each calculation 204 has been computed in an instance of step 414 and the result is stored. In the case where threshold values are associated with each calculation 204, the result for a calculation can be an indication as to whether the calculation is positive, negative, or indeterminate.

Consider the case where a model 202 includes five calculations (tests) 204. There will be five rows in calculation results table 318, one for each of the five calculations 204. Each of these five rows will include a result code. In this user case scenario, each result code is either positive, negative, or indeterminate. Next, the aggregation algorithm associated with the model 202 will specify how these five result codes are to be combined in order to characterize the model 202. For instance, the aggregation algorithm can specify that the five result codes are to be combined in a voting scheme where the model 202 is considered positive (characterized as positive) if more of the computed calculations in the model are positive than are negative.

One example of an aggregation algorithm 214 is a voting scheme where the model 202 is characterized as positive if more of the calculations in the model are positive, when computed, than are negative. For example, consider the case in which a calculation algorithm 212 is applied to the calculations of Table 1, above, and that calculations 1 and 2 are positive, calculation 3 is indeterminate, and calculation 4 is negative. When this is the result, a model that consists of the calculations in Table 1 will be characterized as positive. However, in some embodiments of the present invention, a weighting scheme can be used where each positive calculation in a model is given a different weight than each negative calculation in the model. For example, each positive calculation in a model can be given a weight of 3.0 and each negative calculation in a model can be given a weight of 1.0. In this weighting scheme, a model will be characterized as positive even when the model consists of one positive calculation and two negative calculations.

In preferred embodiments, each characterized model yields a likelihood that a biological specimen or organism has a biological feature represented by the model. This likelihood represents a model score for the computed model. In other words, each characterized model produces a model characterization (e.g., model score) that indicates whether a test organism of a species or a test biological specimen from the organism of a species is a member of a biological sample class. In some embodiments, the higher a model score, the more likely it is that the biological specimen or organism whose cellular constituent values were used to compute the model (i) has the biological feature represented by the model or (ii) is a member of the biological sample class represented by the model. In some embodiments, a model determines whether it is extremely likely, likely, indeterminate, not likely, or very unlikely that a biological specimen or organism has the biological feature associated with the model or is a member of a biological sample class represented by the test. In some embodiments, the biological feature represented by a model is sensitivity and/or resistance to a therapy combination. In some embodiments, the biological feature represented by a model is metastatic potential of a particular disease and/or likelihood of recurrence of the disease in a biological organism. In some embodiments, the biological sample class represented by a model is a cancer and/or any of the exemplary biological features represented in Section 5.4. In embodiments that track likelihood of recurrence of the disease, a model may score as "sensitive", "low risk", or "high risk", etc. In embodiments that track metastatic potential of a disease, a model may score as "malignant", "inconclusive", or "non malignant", etc. In embodiments that evaluate aggressiveness of a disease, a model may score as "aggressive", "inconclusive", or "indolent", etc.

Steps 422 and 424.

In step 422, a determination is made as to whether all the models in the set of models that are to be run (computed) on a given cellular constituent abundance file have been run. If not (422—No) process control returns to step 406 where another model 202 is selected. If all the models have been run, then the results are reported (step 424). In some embodiments, the results that are reported are a characterization of each model in a plurality of models.

In typical embodiments, the results that are reported are a characterization of each model 202 in the set of models that have been run. Each respective model 202 that has been run is characterized in accordance with the respective aggregation algorithm 214 for the model. In typical embodiments, results are reported to the remote client computer that submitted the original cellular constituent abundance file. Exemplary reports made in step 424 are described in Section 5.3.

5.3. Exemplary Results

In some embodiments, the report provided in step 424 is sent from computer 20 to a remote computer that originated the cellular constituent characteristic data file in step 402 of FIG. 4. In some embodiments, the report has a header that provides the following information:

an address of the lab requesting computation of one or models;

a unique order identifier for the request;

a unique specimen identifier that identifies the specimen submitted;

an identifier that identifies the microarray format used to measure cellular constituent characteristic data;

a date the cellular constituent characteristic data file was submitted to computer 20 in step 402;

a date the report of step 424 was generated;

an identifier that identifies the patient represented by the cellular constituent characteristic data file;

a description of the biological specimen from which cellular constituent characteristic data was obtained for the cellular constituent characteristic file; and/or an identity of a physician or other health care professional that ordered the models to be run on the biological specimen.

Tables 3 and 4 below collectively represent an example of a report that is provided for a prostate suite of models. Each row in Tables 3 and 4 represent a different model. In Table 3, each reported model has a clinical test name that provides an indication of what the model tests, one or more references to a research article (or other form of clinical test) that provides the scientific basis for selection of cellular constituents to test the mode, a model result, and a clinical description of the model result. Table 3 provides models that indicate either (i) the degree of likelihood that a patient will suffer from a recurrence of prostate cancer or (ii) the sensitivity of the patient to a particular form of treatment. Table 4 differs from Table 3 in that each row (model) of Table 4 represents a confirmation test that confirms whether or not a patient has prostate cancer.

TABLE 3

Prostate cancer suite/clinical tests.

| CLINICAL TESTS | REFERENCE | RESULT | DESCRIPTION |
|---|---|---|---|
| Androgen Ablation-resistance | Holzbeierlein-Gerald 2004 | Sensitive | Expression signature inconsistent with androgen ablation-resistance |
| Likelihood of Recurrence | LaTulippe-Gerald 2002 | Low risk | Expression signature consistent with low risk of recurrence |
| Likelihood of Recurrence | Singh-Sellers 2002 | Low risk | Expression signature consistent with low risk of recurrence |
| Likelihood of Recurrence | Febbo-Sellers 2003 | Low risk | Expression signature consistent with low risk of recurrence |
| Likelihood of Recurrence | Henshall-Sutherland 2003 | Low risk | Expression signature consistent with low risk of recurrence |
| Likelihood of Recurrence | Lapointe-Pollack 2004 | Low risk | Expression signature consistent with low risk of recurrence |

TABLE 4

Prostate cancer suite/confirmation tests.

| CONFIRMATION TESTS | REFERENCE | RESULT | DESCRIPTION |
|---|---|---|---|
| Benign vs. Malignant | Ernst-Grone 2002 | Malignant | Expression signature consistent with malignant cells |
| Benign vs. Malignant | Welsh-Hampton 2001 | Inconclusive | Expression signature inconclusive with respect to malignancy |
| Benign vs. Malignant | Magee-Milbrandt 2001 | Malignant | Expression signature consistent with malignant cells |
| Site of Origin: Prostate | Su-Hampton 2001 | Prostate | Expression signature consistent with primary prostate carcinoma. |

Tables 5 and 6 describe chemosensitivity models that are found in another type of report that is sent in step 424 in another instance of the present invention.

TABLE 5

Chemosensivity model report.

| CHEMO-SENSITIVITY TESTS | REFERENCE | RESULT | DESCRIPTION |
|---|---|---|---|
| Vinca alkaloid: Camptothecin | PathWork 2004 | Sensitive | Gene expression consistent with camptothecin sensitivity |
| Vinca alkaloid: Irinotecan | PathWork 2004 | Sensitive | Gene expression consistent with irinotecan sensitivity |
| Vinca alkaloid: Vincristine | PathWork 2004 | Resistant | Gene expression consistent with vincristine resistance |
| Vinca alkaloid: Vinblastine | PathWork 2004 | Resistant | Gene expression consistent with vinblastine resistance |
| Taxane: Paclitaxel | PathWork 2004 | Resistant | Gene expression consistent with paclitaxel resistance |

TABLE 5-continued

Chemosensivity model report.

| CHEMO-SENSITIVITY TESTS | REFERENCE | RESULT | DESCRIPTION |
|---|---|---|---|
| Taxane: Docetaxel | PathWork 2004 | Sensitive | Gene expression consistent with docetaxel sensitivity |
| Antibiotic: Actinomycin D | PathWork 2004 | Resistant | Gene expression consistent with actinomycin D resistance |
| Antibiotic: Bleomycin | PathWork 2004 | Resistant | Gene expression consistent with bleomycin resistance |
| Antibiotic: Mitomycin C | PathWork 2004 | Resistant | Gene expression consistent with mitomycin C resistance |
| Anthracycline: Doxorubicin | PathWork 2004 | Resistant | Gene expression consistent with doxorubicin resistance |
| Anthracycline: Daunorubicin | PathWork 2004 | Resistant | Gene expression consistent with daunorubicin resistance |
| Antimetabolite: Methotrexate | PathWork 2004 | Resistant | Gene expression consistent with methotrexate resistance |
| Antimetabolite: 5-fluorouracil | PathWork 2004 | Sensitive | Gene expression consistent with 5-fluorouracil sensitivity |
| Antimetabolite: Cytarabine | PathWork 2004 | Resistant | Gene expression consistent with cytarabine resistance |
| Antimetabolite: Gemcitabine | PathWork 2004 | Sensitive | Gene expression consistent with gemcitabine sensitivity |
| Antimetabolite: 6-thioguanine | PathWork 2004 | Resistant | Gene expression consistent with 6-thioguanine resistance |
| Antimetabolite: 6-mercapto-purine | PathWork 2004 | Resistant | Gene expression consistent with 6-mercaptopurine resistance |

TABLE 6

Chemosensivity Model.

| CHEMO-SENSITIVITY TESTS | REFERENCE | RESULT | DESCRIPTION |
|---|---|---|---|
| DNA alkylator: Cisplatin | PathWork 2004 | Sensitive | Gene expression consistent with cisplatin sensitivity |
| Interferon: Interferon-α | PathWork 2004 | Resistant | Gene expression consistent with interferon-α resistance |
| Interferon: Interferon-β | PathWork 2004 | Resistant | Gene expression consistent with interferon-β resistance |
| Interferon: Interferon-γ | PathWork 2004 | Resistant | Gene expression consistent with interferon-γ resistance |
| Other: STI 571 | PathWork 2004 | Resistant | Gene expression consistent with STI 571 resistance |
| Other: L-asparaginase | PathWork 2004 | Resistant | Gene expression consistent with L-asparaginase resistance |

Tables 7 and 8 describe colorectal models that are found in another type of report that is sent in step 424 in another instance of the present invention.

TABLE 7

Colorectal model report.

| CLINICAL TESTS | REFERENCE | RESULT | DESCRIPTION |
|---|---|---|---|
| Chemosensitivity: 5FU | Takeshi-Fukushima 2001 | Resistant | Expression signature consistent with 5FU resistant cancers |
| Chemosensitivity: 5FU/RTX | Farrugia-Jackman 2003 | Sensitive | Expression signature consistent with 5FU/RTX sensitive cancers |
| Chemosensitivity: 5FU/CPT | Mariadason-Augenlicht 2003 | Sensitive | Expression signature consistent with 5FU/CPT sensitive cancers |
| Chemosensitivity: cisplatin | Huerta-Heber 2003 | Inconclusive | Expression signature inconclusive with respect to cisplatin sensitivity |
| Metastatic Potential | Li-Furukawa 2004 | Low risk | Expression signature consistent with low risk for metastasis |
| Metastatic Potential | Hedge-Quakenbush 2001 | Low risk | Expression signature consistent with low risk for metastasis |

TABLE 8

Colorectal model report.

| CONFIRMATION TESTS | REFERENCE | RESULT | DESCRIPTION |
|---|---|---|---|
| Benign vs. Malignant | Yamamoto-Imai 2002 | Malignant | Expression signature consistent with malignancy |
| Benign vs. Malignant | Zou-Meltzer 2002 | Inconclusive | Expression signature inconclusive with respect to malignancy |
| Adenoma vs. Carcinoma | Lin-Nakamura 2002 | Carcinoma | Expression signature consistent with carcinoma |
| Adenoma vs. Carcinoma | Notterman-Levine 2001 | Carcinoma | Expression signature consistent with carcinoma |

TABLE 8-continued

Colorectal model report.

| CONFIRMATION TESTS | REFERENCE | RESULT | DESCRIPTION |
|---|---|---|---|
| Site of Origin: Colorectal | Su-Hampton 2001 | Colorectal | Expression signature consistent with primary colorectal carcinoma. |

Table 9 describes a site of origin suite of models that is found in another type of report that is sent in step 424 in another embodiment of the present invention.

TABLE 9

Site of origin report.

| SITE OF ORIGIN | PATHWORK INDEX | PREDICTIVE SIGNIFICANCE | |
|---|---|---|---|
| | | LOW | HIGH |
| Colorectum | +32 | | ♦ |
| Lung | +12 | | ♦ |
| Stomach | −42 | ♦ | |
| Liver | −42 | ♦ | |
| Kidney | −88 | ♦ | |
| Breast | −88 | ♦ | |
| Ovary | −88 | ♦ | |
| Bladder | −88 | ♦ | |
| Pancreas | −100 | ♦ | |
| Prostate | −100 | ♦ | |

5.4. Exemplary Biological Features

The present invention can be used to develop models that determine whether a biological specimen has any of a plurality of biological features. In other words, the present invention can be used to develop models that indicate whether a test organism of a species or a test biological specimen from an organism of a species is a member of a biological sample class. A broad array of biological features (e.g. biological sample classes) is contemplated. In one example, two respective biological features are (i) a wild type state and (ii) a diseased state. In another example two respective biological features are (i) a first diseased state and a second diseased state. In still another example, two respective biological features are (i) a drug respondent state and (ii) a drug nonrespondent state. In such instances, a first model 202 tests for the absence or presence of the first biological sample feature and a second model 202 tests for the absence or presence of the second biological feature. The present invention is not limited to instances where a sample is tested for the absence or presence of only two biological features. Indeed any number of biological features (e.g., one biological feature, two or more biological features, between three and ten biological features, between five and twenty biological features, more than twenty-five biological features, etc.) can be tested using the methods, computers, and computer program products of the present invention. In such instances, a different model 202 is typically used to test for the presence or absence of each such biological feature (e.g., to determine whether the specimen is a member of biological sample class characterized by the presence of the feature or is, alternatively, a member of a biological sample class characterized by the absence of the feature). In some embodiments, multiple models test for the absence or presence of the same biological features. In other words, multiple models test to determine whether a biological sample is a member of a particular biological sample class. This section describes exemplary biological features. Organisms a given biological feature can be considered members of a corresponding biological sample class.

5.4.1 Breast Cancer

Pusztai et al. Several different adjuvant chemotherapy regimens are used in the treatment of breast cancer. Not all regimens may be equally effective for all patients. Currently it is not possible to select the most effective regimen for a particular individual. One accepted surrogate of prolonged recurrence-free survival after chemotherapy in breast cancer is complete pathologic response (pCR) to neoadjuvant therapy. Pusztai et al., ASCO 2003 abstract 1 report the discovery of a gene expression profile that predicts pCR after neoadjuvant weekly paclitaxel followed by FAC sequential chemotherapy (T/FAC). The Pusztai et al. predictive markers were generated from fine needle aspirates of 24 early stage breast cancers. Six of the 24 patients achieved pCR (25 percent). In Pusztai et al., RNA from each sample were profiled on cDNA microarrays of 30,000 human transcripts. Differentially expressed genes between the pCR and residual disease (RD) groups were selected by signal-to-noise-ratio. Several supervised learning methods were evaluated to define the best class prediction algorithm and the optimal number of genes needed for outcome prediction using leave-one out cross validation. A support vector machine using five genes (3 ESTs, nuclear factor 1/A, and histone acetyltransferase) yielded the greatest estimated accuracy. This predictive marker set was tested on independent cases receiving T/FAC neoadjuvant therapy. Pusztai et al. reported results for 21 patients included in the validation. The overall accuracy of the Pusztai et al. response prediction based on gene expression profile was 81 percent. The overall specificity was 93 percent. The sensitivity was 50 percent (three of the six pCR were misclassified as RD). Pusztai et al. found that patients predicted to have pCR to T/FAC preoperative chemotherapy had a 75 percent chance of experiencing pCR compared to 25-30 percent that is expected in unselected patients. The Pusztai et al. findings can be used to build a model 202 that can then be used to help physicians to select individual patients who are most likely to benefit from T/FAC adjuvant chemotherapy.

Cobleigh et al. Breast cancer patients with ten or more positive nodes have a poor prognosis, yet some survive long-term. Cobleigh et al., ASCO 2003 abstract 3415 sought to identify predictors of distant disease-free survival (DDFS) in this high risk group of patients. Patients with invasive breast cancer and ten or more positive nodes diagnosed from 1979 to 1999 were identified. RNA was extracted from three 10 micron sections and expression was quantified for seven reference genes and 185 cancer-related genes using RT-PCR. The genes were selected based on the results of published literature and microarray experiments. A total of 79 patients were studied. Fifty-four percent of the patients received hormonal therapy and eighty percent received chemotherapy. Median follow-up was 15.1 yrs. As of August 2002, 77 percent of patients had distant recurrence or breast cancer death. Univariate Cox survival analysis of the clinical variables indicated that the number of nodes involved was significantly associated with DDFS ($p=0.02$). Cobleigh et al. applied a multivariate model including age, tumor size, involved nodes, tumor grade, adjuvant hormonal therapy, and chemotherapy that accounted for 13 percent of the variance in DDFS time. Univariate Cox survival analysis of the 185 cancer-related genes indicated that a number of genes were associated with DDFS (5 with $p<0.01$; 16 with $p<0.05$). Higher expression was associated with shorter DDFS ($p<0.01$) for the HER2 adaptor Grb7 and the macrophage marker CD68. Higher expression was associated with longer DDFS (p<0.01) for TP53BP2 (tumor protein p53-binding protein 2), PR, and Bcl2. A multivariate model including five genes accounted for 45 percent of the variance in DDFS time. Multivariate analysis also indicated that gene expression is a significant predictor after controlling for clinical variables. The Cobleigh et al. findings can be used to build a model 202 that can then be used to help determine which patients are likely associated with DDFS and that are not likely associated with DDFS.

van't Veer. Breast cancer patients with the same stage of disease can have markedly different treatment responses and overall outcome. Predictors for metastasis (a poor outcome), lymph node status and histological grade, for example fail to classify accurately breast tumors according to their clinical behavior. To address this shortcoming van't Veer 2002, Nature 415, 530-535, used DNA microanalysis on primary breast tumors of 117 patients, and applied supervised classification to identify a gene expression signature strongly predictive of a short interval to distant metastases ('poor prognosis' signature) in patients without tumor cells in local lymph nodes at diagnosis (lymph node negative). In addition van't Veer established a signature that identifies tumors of BRCA1 carriers. The van't Veer findings can be used to build a model 202 that can then be used to help determine patient prognosis.

Other references. A representative sample of additional breast cancer studies that can be used to build models 202 for detecting breast cancer include, but are not limited to, Soule et al., ASCO 2003 abstract 3466; Ikeda et al., ASCO 2003 abstract 34; Schneider et al., 2003, British Journal of Cancer 88, p. 96; Long et al. ASCO 2003 abstract 3410; and Chang et al., 2002, PeerView Press, Abstract 1700, "Gene Expression Profiles for Docetaxel Chemosensitivity."

5.4.2 Lung Cancer

Rosell-Costa et al. ERCC1 mRNA levels correlate with DNA repair capacity (DRC) and clinical resistance to cisplatin. Changes in enzyme activity and gene expression of the M1 or M2 subunits of ribonucleotide reductase (RR) are observed during DNA repair after gemcitabine damage. Rosell-Costa et al., ASCO 2003 abstract 2590 assessed ERCC1 and RRM1 mRNA levels by quantitative PCR in RNA isolated from tumor biopsies of 100 stage IV (NSCLC) patients included in a trial of 570 patients randomized to gem/cis versus gem/cis/vrb vs gem/vrb followed by vrb/ifos (Alberola et al. ASCO 2001 abstract 1229). ERCC1 and RRM1 data were available for 81 patients. Overall response rate, time to progression (TTP) and median survival (MS) for these 81 patients were similar to results for all 570 patients. A strong correlation between ERCC1 and RRM1 levels was found (P=0.00001). Significant differences in outcome according to ERCC1 and RRM1 levels were found in the gem/cis arm but not in the other arms. In the gem/cis arm, TTP was 8.3 months for patients with low ERCC1 and 5.1 months for patients with high ERCC1 (P=0.07), 8.3 months for patients with low RRM1 and 2.7 months for patients with high RRM1 (P=0.01), 10 months for patients with low ERCC1 & RRM1 and 4.1 months for patients with high ERCC1 & RRM1 (P=0.009). MS was 13.7 months for patients with low ERCC1 and 9.5 months for patients with high ERCC1 (P=0.19), 13.7 months for patients with low RRM1 and 3.6 months for patients with high RRM1 (P=0.009), not reached for patients with low ERCC1 & RRM1 and 6.8 months for patients with high ERCC1 & RRM1 (P=0.004). Patients with low ERCC1 and RRM1 levels, indicating low DRC, are ideal candidates for gem/cis, while patients with high levels have poorer outcome. Accordingly, ratios that include ERCC1 & RRM1 scan be used to build models 202 that determine what kind of therapy should be given to lung cancer patients.

Hayes et al. Despite the high prevalence of lung cancer, a robust stratification of patients by prognosis and treatment response remains elusive. Initial studies of lung cancer gene expression arrays have suggested that previously unrecognized subclasses of adenocarcinoma may exist. These studies have not been replicated and the association of subclass with clinical outcomes remains incomplete. For the purpose of comparing subclasses suggested by the three largest case series, their gene expression arrays comprising 366 tumors and normal tissue samples were analyzed in a pooled data set by Hayes et al., ASCO 2003 abstract 2526. The common set of expression data was re-scaled and gene filtering was employed to select a subset of genes with consistent expression between replicate pairs yet variable expression across all samples. Hierarchical clustering was performed on the common data set and the resultant clusters compared to those proposed by the authors of the original manuscripts. In order to make direct comparisons to the original classification schemes, a classifier was constructed and applied to validation samples from the pool of 366 tumors. In each step of the analysis, the clustering agreement between the validation and the originally published classes was statistically significant. In an additional validation step, the lists of genes describing the originally published subclasses were compared across classification schemes. Again there was statistically significant overlap in the lists of genes used to describe adenocarcinoma subtypes. Finally, survival curves demonstrated one subtype of adenocarcinoma with consistently decreased survival. The Hayes et al. analyses helps to establish that reproducible adenocarcinoma subtypes can be described based on mRNA expression profiling. Accordingly the results of Hayes et al. can be used to build models 202 that can be used to identify adenocarcinoma subtypes.

5.4.3 Prostate Cancer

Li et al. TAXOTERE shows anti-tumor activity against solid tumors including prostate cancer. However, the molecular mechanism(s) of action of TAXOTERE have not been fully elucidated. In order to establish the molecular mechanism of action of TAXOTERE in both hormone insensitive (PC3) and sensitive (LNCaP) prostate cancer cells comprehensive gene expression profiles were obtained by using AFFYMETRIX Human Genome U133A array. See Li et al. ASCO 2003 abstract 1677. The total RNA from cells untreated and treated with 2 nM TAXOTERE for 6, 36, and 72 hours was subjected to microarray analysis and the data were analyzed using Microarray Suite and Data Mining, Cluster and TreeView, and Onto-express software. The alterations in the expression of genes were observed as early as six hours, and more genes were altered with longer treatments. Additionally, TAXOTERE exhibited differential effects on gene expression profiles between LNCaP and PC3 cells. A total of 166, 365, and 1785 genes showed >2 fold change in PC3 cells after 6, 36, and 72 hours, respectively compared to 57, 823, and 964 genes in LNCaP cells. Li et al. found no effect on androgen receptor, although up-regulation of several genes involved in steroid-independent AR activation (IGFBP2, FGF13, EGFR, etc) was observed in LNCaP cells. Clustering analysis showed down-regulation of genes for cell proliferation and cell cycle (cyclins and CDKs, Ki-67, etc), signal transduction (IMPA2, ERBB21P, etc), transcription factors (HMG-2, NFYB, TRIP13, PIR, etc), and oncogenesis (STK15, CHK1, Survivin, etc.) in both cell lines. In contrast, TAXOTERE up-regulated genes that are related to induction of apoptosis (GADD45A, FasApo-1, etc), cell cycle arrest (p21CIP1, p27KIP1, etc) and tumor suppression. From these results, Li et al. concluded that TAXOTERE caused alterations of a large number of genes, many of which may contribute to the molecular mechanism(s) by which TAXOTERE affects prostate cancer cells. This information could be further exploited to devise strategies to optimize therapeutic effects of TAXOTERE for the treatment of metastatic prostate cancer.

Using the results described in this section, models 202 that stratify patients into groups that will have a varying degree of response to Taxotere and related treatment regimens (e.g. a first biological feature that is highly responsive to Taxotere, a second biological feature that is not responsive to Taxotere, etc.) can be developed. In another approach, biological features can be developed based, in part, on Cox-2 expression in order to serve as a survival predictor in stage D2 prostate cancer.

5.4.4. Colorectal Cancer

Kwon et al. To identify a set of genes involved in the development of colorectal carcinogenesis, Kwon et al. ASCO 2003 abstract 1104 analysed gene-expression profiles of colorectal cancer cells from twelve tumors with corresponding noncancerous colonic epithelia by means of a cDNA microarray representing 4,608 genes. Kwon et al. classified both samples and genes by a two-way clustering analysis and identified genes that were differentially expressed between cancer and noncancerous tissues. Alterations in gene expression levels were confirmed by reverse-transcriptase PCR (RT-PCR) in selected genes. Gene expression profiles according to lymph node metastasis were evaluated with a supervised learning technique. Expression change in more than 75 percent of the tumors was observed for 122 genes, i.e., 77 up-regulated and 45 down-regulated genes. The most frequently altered genes belonged to functional categories of signal transduction (19 percent), metabolism (17 percent), cell structure/motility (14 percent), cell cycle (13 percent) and gene protein expression (13 percent). The RT-PCR analysis of randomly selected genes showed consistent findings with those in cDNA microarray. Kwon et al. could predict lymph node metastasis for 10 out of 12 patients with cross-validation loops. The results of Kwon et al. can be used to develop a model 202 for determining whether a patient has colorectal cancer. Furthermore, the results of Kwon et al. can be extended to identify subclasses of colorectal cancer.

Additional studies that can be used to develop models 202 for colorectal cancer (including models that identify a biological specimen as having colorectal cancer and possibly additional models that predict subgroups of colorectal cancer) include, but are not limited to Nasir et al., 2002, In Vivo. 16, p. 501 in which research that finds elevated expression of COX-2 has been associated with tumor induction and progression is summarized, as well as Longley et al., 2003 Clin. Colorectal Cancer. 2, p. 223; McDermott et al., 2002, Ann Oncol. 13, p. 235; and Longley et al., 2002, Pharmacogenomics J. 2, p. 209.

5.4.5. Ovarian Cancer

Spentzos et al. To identify expression profiles associated with clinical outcomes in epithelial ovarian cancer (EOC), Spentzos et al. ASCO 2003 abstract 1800 evaluated 38 tumor samples from patients with EOC receiving first-line platinum/taxane-based chemotherapy. RNA probes were reverse-transcribed, fluorescent-labeled, and hybridized to oligonucleotide arrays containing 12675 human genes and expressed sequence tags. Expression data were analyzed for signatures predictive of chemosensitivity, disease-free survival (DFS) and overall survival (OS). A Bayesian model was used to sort the genes according to their probability of differential expression between tumors of different chemosensitivity and survival. Genes with the highest probability of being differentially expressed between tumor subgroups with different outcome were included in the respective signature. Spentzos et al. found one set of genes that were overexpressed in chemoresistant tumors and another set of genes that were overexpressed in chemosensitive tumors. Spentzos et al. found 45 genes that were overexpressed in tumors associated with short disease free survival (DFS) and 18 genes that were overexpressed in tumors associated with long DFS. These genes separated the patient population into two groups with median DFS of 7.5 and 30.5 months (p<0.00001). Spentzos et al. found 20 genes that were overexpressed in tumors with short overall survival (OS) and 29 genes that were overexpressed in genes with long OS (median OS of 22 and 40 months, p=0.00008). The overexpressed genes identified by Spentzos et al. can be used to build models 202 that classify a biological specimen into biological classes such as chemoresistant ovarian cancer, chemosensitive ovarian cancer, short DFS ovarian cancer, long DFS ovarian cancer, short OS ovarian cancer and long OS ovarian cancer.

Additional studies that can be used to develop models 202 for ovarian cancer include, but are not limited to, Presneau et al., 2003, Oncogene 13, p. 1568; and Takano et al. ASCO 2003 abstract 1856.

5.4.6 Bladder Cancer

Wulfing et al. Cox-2, an inducible enzyme involved in arachidonate metabolism, has been shown to be commonly overexpressed in various human cancers. Recent studies have revealed that Cox-2 expression has prognostic value in patients who undergo radiation or chemotherapy for certain tumor entities. In bladder cancer, Cox-2 expression has not been well correlated with survival data is inconsistent. To address this, Wulfing et al. ASCO 2003 abstract 1621 studied 157 consecutive patients who had all undergone radical cystectomy for invasive bladder cancer. Of these, 61 patients had received cisplatin-containing chemotherapy, either in an adjuvant setting or for metastatic disease. Standard immunohistochemistry was performed on paraffin-embedded tissue blocks applying a monoclonal Cox-2 antibody. Semiquantitative results were correlated to clinical and pathological data, long-term survival rates (3-177 months) and details on chemotherapy. Twenty six (16.6 percent) cases were Cox-2-negative. From all positive cases (n=131, 83.4 percent), 59 (37.6 percent) showed low, 53 (33.8 percent) moderate and 19 (12.1 percent) strong Cox-2 expression. Expression was independent of TNM-Staging and histological grading. Cox-2 expression correlated significantly with the histological type of the tumors (urothelial vs. squamous cell carcinoma; P=0.01). In all investigated cases, Kaplan-Meier analysis did not show any statistical correlation to overall and disease free survival. However, by subgroup analysis of those patients who had cisplatin-containing chemotherapy, Cox-2-expression was significantly related to poor overall survival time (P=0.03). According to Wulfing et al., immunohistochemical overexpression of Cox-2 is a very common event in bladder cancer. Patients receiving chemotherapy seem to have worse survival rates when overexpressing Cox-2 in their tumors. Therefore, Wulfing et al. reasoned that Cox-2 expression could provide additional prognostic information for patients with bladder cancer treated with cisplatin-based chemotherapy regimens and that this could be the basis for a more aggressive therapy in individual patients or a risk-adapted targeted therapy using selective Cox-2-inhibitors. The results of Wulfing et al. can be used to develop a model 202 that stratifies a bladder cancer population into treatment groups.

5.4.7 Gastric Cancer

Terashima et al. In order to detect the chemoresistance-related gene in human gastric cancer, Terashima et al., ASCO 2003 abstract 1161 investigated gene expression profiles using DNA microarray and compared the results with in vitro drug sensitivity. Fresh tumor tissue was obtained from a total of sixteen patients with gastric cancer and then examined for gene expression profile using GeneChip Human U95Av2 array (Affymetrix, Santa Clara, Calif.), which includes 12,000 human genes and EST sequences. The findings were compared with the results of in vitro drug sensitivity determined by a ATP assay. The investigated drugs and drug concentrations were cisplatin (CDDP), doxorubicin (DOX), mitomycin C (MMC), etoposide (ETP), irinotecan (CPT; as SN-38), 5-fluoruuracil (5-FU), doxifluridine (5'-DFUR), paclitaxel (TXL) and docetaxel (TXT). Drug was added at a concentration of $C_{max}$ of each drug for 72 hours. Drug sensitivity was expressed as the ratio of the ATP content in drug treated group to control group (T/C percent). Pearson correlation between the amount of relative gene expression and T/C percent was evaluated and clustering analysis was also performed y using genes selected by the correlation. From these analyses, 51 genes in CDDP, 34 genes in DOX, 26 genes in MMC, 52 genes in ETP, 51 genes in CPT, 85 genes in 5-FU, 42 genes in 5'-DFUR, 11 genes in TXL and 32 genes in TXT were up-regulated in drug resistant tumors. Most of these genes were related to cell growth, cell cycle regulation, apoptosis, heat shock protein or ubiquitin-proteasome pathways. However, several genes, such as ribosomal proteins, CD44 and elongation factor alpha, were specifically up-regulated in each drug-resistant tumors. The up-regulated genes identified by Terashima et al. can be used to develop a model 202 that not only diagnoses patients with gastric cancer, but provides an indication of whether the patient has a drug-resistant gastric tumor and, if so, which kind of drug-resistant tumor.

Additional references that can be used to develop models 202 for gastric cancer include, but are not limited to Kim et al. ASCO 2003 abstract 560; Arch-Ferrer et al. ASCO 2003 abstract 1101; Hobday ASCO 2003 abstract 1078; Song et al. ASCO 2003 abstract 1056 (overexpression of the Rb gene is an independent prognostic factor for predicting relapse free survival); Leichman et al., ASCO 2003 abstract 1054 (thymidylate synthase expression as a predictor of chemobenefit in esophageal/gastric cancer).

5.4.8 Rectal Cancer

Lenz et al. Local recurrence is a significant clinical problem in patients with rectal cancer. Accordingly, Lenz et al. ASCO 2003 abstract 1185 sought to establish a genetic profile that would predict pelvic recurrence in patients with rectal cancer treated with adjuvant chemoradiation. A total of 73 patients with locally advanced rectal cancer (UICC stage II and III), 25 female, 48 male, median age 52.1 years, were treated from 1991-2000. Histological staging categorized 22 patients as stage T2, 51 as stage T3. A total of 35 patients were lymph node negative, 38 had one or more lymph node metastases. All patients underwent cancer resection, followed by 5-FU plus pelvic radiation. RNA was extracted from formal in-fixed, paraffin-embedded, laser-capture-microdissected tissue. Lenz et al. determined mRNA levels of genes involved in the SFU pathway (TS, DPD), angiogenesis (VEGF), and DNA repair (ERCC1, RAD51) in tumor and adjacent normal tissue by quantitative RT-PCR (Taqman). Lenz et al. found a significant association between local tumor recurrence and higher m-RNA expression levels in adjacent normal tissue of ERCC1 and TS suggest that gene expression levels of target genes of the 5-FU pathways as well as DNA repair and angiogenesis may be useful to identify patients at risk for pelvic recurrence. The results of Lenz et al. can be used to develop a model 202 that identifies patients at risk for pelvic recurrence.

5.4.9 Additional Exemplary Biological Features

Additional representative biological features include, but are not limited to, acne, acromegaly, acute cholecystitis, Addison's disease, adenomyosis, adult growth hormone deficiency, adult soft tissue sarcoma, alcohol dependence, allergic rhinitis, allergies, alopecia, alzheimer disease, amniocentesis, anemia in heart failure, anemias, angina pectoris, ankylosing spondylitis, anxiety disorders, arrhenoblastoma of ovary, arrhythmia, arthritis, arthritis-related eye problems, asthma, atherosclerosis, atopic eczema atrophic vaginitis, attention deficit disorder, attention disorder, autoimmune diseases, balanoposthitis, baldness, bartholins abscess, birth defects, bleeding disorders, bone cancer, brain and spinal cord tumors, brain stem glioma, brain tumor, breast cancer, breast cancer risk, breast disorders, cancer, cancer of the kidney, cardiomyopathy, carotid artery disease, carotid endarterectomy, carpal tunnel syndrome, cerebral palsy, cervical cancer, chancroid, chickenpox, childhood nephrotic syndrome, chlamydia, chronic diarrhea, chronic heart failure, claudication, colic, colon or rectum cancer, colorectal cancer, common cold, condyloma (genital warts), congenital goiters, congestive heart failure, conjunctivitis, corneal disease, corneal ulcer, coronary heart disease, cryptosporidiosis, Cushings syndrome, cystic fibrosis, cystitis, cystoscopy or ureteroscopy, De Quervains disease, dementia, depression, mania, diabetes, diabetes insipidus, diabetes mellitus, diabetic retinopathy, Down syndrome, dysmenorrhea in the adolescent, dyspareunia, ear allergy, ear infection, eating disorder, eczema, emphysema, endocarditis, endometrial cancer, endometriosis, eneuresis in children, epididymitis, epilepsy, episiotomy, erectile dysfunction, eye cancer, fatal abstraction, fecal incontinence, female sexual dysfunction, fetal abnormalities, fetal alcohol syndrome, fibromyalgia, flu, folliculitis, fungal infection, gardnerella vaginalis, genital candidiasis, genital herpes, gestational diabetes, glaucoma, glomerular diseases, gonorrhea, gout and pseudogout, growth disorders, gum disease, hair disorders, halitosis, Hamburger disease, hemophilia, hepatitis, hepatitis b, hereditary colon cancer, herpes infection, human placental lactogen, hyperparathyroidism, hypertension, hyperthyroidism, hypoglycemia, hypogonadism, hypospadias, hypothyroidism, hysterectomy, impotence, infertility, inflammatory bowel disease, inguinal hernia, inherited heart irregularity, intraocular melanoma, irritable bowel syndrome, Kaposis sarcoma, leukemia, liver cancer, lung cancer, lung disease, malaria, manic depressive illness, measles, memory loss, meningitis in children, menorrhagia, mesothelioma, microalbumin, migraine headache, mittelschmerz, mouth cancer, movement disorders, mumps, Nabothian cyst, narcolepsy, nasal allergies, nasal cavity and paranasal sinus cancer, neuroblastoma, neurofibromatosis, neurological disorders, newborn jaundice, obesity, obsessive-compulsive disorder, orchitis or epididymitis, orofacial myofunctional disorders, osteoarthritis, osteoporosis, osteoporosis, osteosarcoma, ovarian cancer, ovarian cysts, pancreatic cancer, paraphimosis, Parkinson disease, partial epilepsy, pelvic inflammatory disease, peptic ulcer, peripartum cardiomyopathy, peyronie disease, polycystic ovary syndrome, preeclampsia, premenstrual syndrome, priapism, prolactinoma, prostate cancer, psoriasis, rheumatic fever, salivary gland cancer, SARS, sexually transmitted diseases, sexually transmitted enteric infections, sexually transmitted infections, Sheehans syndrome, sinusitis, skin cancer, sleep disorders, smallpox, smell disorders, snoring, social phobia, spina bifida, stomach cancer, syphilis, testicular cancer, thyroid cancer, thyroid disease, tonsillitis, tooth disorders, trichomoniasis, tuberculosis, tumors, type II diabetes, ulcerative colitis, urinary tract infections, urological cancers, uterine fibroids, vaginal cancer, vaginal cysts, vulvodynia, and vulvovaginitis.

5.5 Transcriptional State Measurements

This section provides some exemplary methods for measuring the expression level of genes, which are one type of cellular constituent. One of skill in the art will appreciate that this invention is not limited to the following specific methods for measuring the expression level of genes in each organism in a plurality of organisms.

5.5.1 Transcript Assay Using Microarrays

The techniques described in this section include the provision of polynucleotide probe arrays that can be used to provide simultaneous determination of the expression levels of a plurality of genes. These techniques further provide methods for designing and making such polynucleotide probe arrays.

The expression level of a nucleotide sequence in a gene can be measured by any high throughput techniques. However measured, the result is either the absolute or relative amounts of transcripts or response data, including but not limited to values representing abundances or abundance ratios. Preferably, measurement of the expression profile is made by hybridization to transcript arrays, which are described in this subsection. In one embodiment, "transcript arrays" or "profiling arrays" are used. Transcript arrays can be employed for analyzing the expression profile in a cell sample and especially for measuring the expression profile of a cell sample of a particular tissue type or developmental state or exposed to a drug of interest.

In one embodiment, an expression profile is obtained by hybridizing detectably labeled polynucleotides representing the nucleotide sequences in mRNA transcripts present in a cell (e.g., fluorescently labeled cDNA synthesized from total cell mRNA) to a microarray. A microarray is an array of positionally-addressable binding (e.g., hybridization) sites on a support for representing many of the nucleotide sequences in the genome of a cell or organism, preferably most or almost all of the genes. Each of such binding sites consists of polynucleotide probes bound to the predetermined region on the support. Microarrays can be made in a number of ways, of which several are described herein below. However produced, microarrays share certain characteristics. The arrays are reproducible, allowing multiple copies of a given array to be produced and easily compared with each other. Preferably, the microarrays are made from materials that are stable under binding (e.g., nucleic acid hybridization) conditions. Microarrays are preferably small, e.g., between 1 cm$^2$ and 25 cm$^2$, preferably 1 to 3 cm$^2$. However, both larger and smaller arrays are also contemplated and may be preferable, e.g., for simultaneously evaluating a very large number or very small number of different probes.

Preferably, a given binding site or unique set of binding sites in the microarray will specifically bind (e.g., hybridize) to a nucleotide sequence in a single gene from a cell or organism (e.g., to exon of a specific mRNA or a specific cDNA derived therefrom).

The microarrays used can include one or more test probes, each of which has a polynucleotide sequence that is complementary to a subsequence of RNA or DNA to be detected. Each probe typically has a different nucleic acid sequence, and the position of each probe on the solid surface of the array is usually known. Indeed, the microarrays are preferably addressable arrays, more preferably positionally addressable arrays. Each probe of the array is preferably located at a known, predetermined position on the solid support so that the identity (e.g., the sequence) of each probe can be determined from its position on the array (e.g., on the support or surface). In some embodiments, the arrays are ordered arrays.

Preferably, the density of probes on a microarray or a set of microarrays is 100 different (e.g., non-identical) probes per 1 cm$^2$ or higher. More preferably, a microarray used in the methods of the invention will have at least 550 probes per 1 cm$^2$, at least 1,000 probes per 1 cm$^2$, at least 1,500 probes per 1 cm$^2$, at least 2,000 probes per 1 cm$^2$, at least 8,000 probes per 1 cm$^2$, or at least 15,000 probes per 1 cm$^2$, or greater. The microarrays used in the invention therefore preferably contain at least 25,000, at least 50,000, at least 100,000, at least 150,000, at least 200,000, at least 250,000, at least 500,000 or at least 550,000 different (e.g., non-identical) probes.

In one embodiment, the microarray is an array (e.g., a matrix) in which each position represents a discrete binding site for a nucleotide sequence of a transcript encoded by a gene (e.g., for an exon of an mRNA or a cDNA derived therefrom). The collection of binding sites on a microarray contains sets of binding sites for a plurality of genes. For example, in various embodiments, the microarrays of the invention can comprise binding sites for products encoded by fewer than 50 percent of the genes in the genome of an organism. Alternatively, the microarrays of the invention can have binding sites for the products encoded by at least 50 percent, at least 75 percent, at least 85 percent, at least 90 percent, at least 95 percent, at least 99 percent or 100 percent of the genes in the genome of an organism. In other embodiments, the microarrays of the invention can have binding sites for products encoded by fewer than 50 percent, by at least 50 percent, by at least 75 percent, by at least 85 percent, by at least 90 percent, by at least 95 percent, by at least 99 percent or by 100 percent of the genes expressed by a cell of an organism. The binding site can be a DNA or DNA analog to which a particular RNA can specifically hybridize. The DNA or DNA analog can be, e.g., a synthetic oligomer or a gene fragment, e.g. corresponding to an exon.

In some embodiments of the present invention, a gene or an exon in a gene is represented in the profiling arrays by a set of binding sites comprising probes with different polynucleotides that are complementary to different sequence segments of the gene or the exon. Such polynucleotides are preferably of the length of 15 to 200 bases, more preferably of the length of 20 to 100 bases, most preferably 40-60 bases. Each probe sequence may also comprise linker sequences in addition to the sequence that is complementary to its target sequence. As used herein, a linker sequence is a sequence between the sequence that is complementary to its target sequence and the surface of support. For example, in preferred embodiments, the profiling arrays of the invention comprise one probe specific to each target gene or exon. However, if desired, the profiling arrays may contain at least 2, 5, 10, 100, or 1000 or more probes specific to some target genes or exons. For example, the array may contain probes tiled across the sequence of the longest mRNA isoform of a gene at single base steps.

In specific embodiments of the invention, when an exon has alternative spliced variants, a set of polynucleotide probes of successive overlapping sequences, i.e., tiled sequences, across the genomic region containing the longest variant of an exon can be included in the exon profiling arrays. The set of polynucleotide probes can comprise successive overlapping sequences at steps of a predetermined base intervals, e.g. at steps of 1, 5, or 10 base intervals, span, or are tiled across, the mRNA containing the longest variant. Such sets of probes therefore can be used to scan the genomic region containing all variants of an exon to determine the expressed variant or variants of the exon to determine the expressed variant or variants of the exon. Alternatively or additionally, a set of polynucleotide probes comprising exon specific probes and/or variant junction probes can be included in the exon profiling array. As used herein, a variant junction probe refers to a probe specific to the junction region of the particular exon variant and the neighboring exon. In some cases, the probe set contains variant junction probes specifically hybridizable to each of all different splice junction sequences of the exon. In other cases, the probe set contains exon specific probes specifically hybridizable to the common sequences in all different variants of the exon, and/or variant junction probes specifically hybridizable to the different splice junction sequences of the exon.

In some cases, an exon is represented in the exon profiling arrays by a probe comprising a polynucleotide that is complementary to the full length exon. In such instances, an exon is represented by a single binding site on the profiling arrays. In some preferred cases, an exon is represented by one or more binding sites on the profiling arrays, each of the binding sites comprising a probe with a polynucleotide sequence that is complementary to an RNA fragment that is a substantial portion of the target exon. The lengths of such probes are normally between 15-600 bases, preferably between 20-200 bases, more preferably between 30-100 bases, and most preferably between 40-80 bases. The average length of an exon is about 200 bases (see, e.g., Lewin, *Genes V*, Oxford University Press, Oxford, 1994). A probe of length of 40-80 allows more specific binding of the exon than a probe of shorter length, thereby increasing the specificity of the probe to the target exon. For certain genes, one or more targeted exons may have sequence lengths less than 40-80 bases. In such cases, if probes with sequences longer than the target exons are to be used, it may be desirable to design probes comprising sequences that include the entire target exon flanked by sequences from the adjacent constitutively spliced exon or exons such that the probe sequences are complementary to the corresponding sequence segments in the mRNAs. Using flanking sequence from adjacent constitutively spliced exon or exons rather than the genomic flanking sequences, i.e., intron sequences, permits comparable hybridization stringency with other probes of the same length. Preferably the flanking sequences used are from the adjacent constitutively spliced exon or exons that are not involved in any alternative pathways. More preferably the flanking sequences used do not comprise a significant portion of the sequence of the adjacent exon or exons so that cross-hybridization can be minimized. In some embodiments, when a target exon that is shorter than the desired probe length is involved in alternative splicing, probes comprising flanking sequences in different alternatively spliced mRNAs are designed so that expression level of the exon expressed in different alternatively spliced mRNAs can be measured.

In some instances, when alternative splicing pathways and/or exon duplication in separate genes are to be distinguished, the DNA array or set of arrays can also comprise probes that are complementary to sequences spanning the junction regions of two adjacent exons. Preferably, such probes comprise sequences from the two exons which are not substantially overlapped with probes for each individual exon so that cross hybridization can be minimized. Probes that comprise sequences from more than one exon are useful in distinguishing alternative splicing pathways and/or expression of duplicated exons in separate genes if the exons occurs in one or more alternative spliced mRNAs and/or one or more separated genes that contain the duplicated exons but not in other alternatively spliced mRNAs and/or other genes that contain the duplicated exons. Alternatively, for duplicate exons in separate genes, if the exons from different genes show substantial difference in sequence homology, it is preferable to include probes that are different so that the exons from different genes can be distinguished.

It will be apparent to one of skill in the art that any of the probe schemes, supra, can be combined on the same profiling array and/or on different arrays within the same set of profiling arrays so that a more accurate determination of the expression profile for a plurality of genes can be accomplished. It will also be apparent to one skilled in the art that the different probe schemes can also be used for different levels of accuracies in profiling. For example, a profiling array or array set comprising a small set of probes for each exon may be used to determine the relevant genes and/or RNA splicing pathways under certain specific conditions. An array or array set comprising larger sets of probes for the exons that are of interest is then used to more accurately determine the exon expression profile under such specific conditions. Other DNA array strategies that allow more advantageous use of different probe schemes are also encompassed.

Preferably, the microarrays used in the invention have binding sites (i.e., probes) for sets of exons for one or more genes relevant to the action of a drug of interest or in a biological pathway of interest. As discussed above, a "gene" is identified as a portion of DNA that is transcribed by RNA polymerase, which may include a 5 untranslated region ("UTR"), introns, exons and a 3 UTR. The number of genes in a genome can be estimated from the number of mRNAs expressed by the cell or organism, or by extrapolation of a well characterized portion of the genome. When the genome of the organism of interest has been sequenced, the number of ORFs can be determined and mRNA coding regions identified by analysis of the DNA sequence. For example, the genome of *Saccharomyces cerevisiae* has been completely sequenced and is reported to have approximately 6275 ORFs encoding sequences longer than 99 amino acid residues in length. Analysis of these ORFs indicates that there are 5,885 ORFs that are likely to encode protein products (Goffeau et al., 1996, *Science* 274: 546-567). In contrast, the human genome is estimated to contain approximately 30,000 to 130,000 genes (see Crollius et al., 2000, *Nature Genetics* 25:235-238; Ewing et al., 2000, *Nature Genetics* 25:232-234). Genome sequences for other organisms, including but not limited to *Drosophila, C. elegans*, plants, e.g., rice and *Arabidopsis*, and mammals, e.g., mouse and human, are also completed or nearly completed. Thus, in preferred embodiments of the invention, an array set comprising in total probes for all known or predicted exons in the genome of an organism is provided. As a non-limiting example, the present invention provides an array set comprising one or two probes for each known or predicted exon in the human genome.

It will be appreciated that when cDNA complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (e.g., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In one embodiment, cDNAs from cell samples from two different conditions are hybridized to the binding sites of the microarray using a two-color protocol. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA derived from each of the two cell types are differently labeled (e.g., with Cy3 and Cy5) so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by the ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exon expressed in the mRNA will decrease.

The use of a two-color fluorescence labeling and detection scheme to define alterations in gene expression has been described in connection with detection of mRNAs, e.g., in Schena et al., 1995, Quantitative monitoring of gene expression patterns with a complementary DNA microarray, *Science* 270:467-470, which is incorporated by reference in its entirety for all purposes. The scheme is equally applicable to labeling and detection of exons. An advantage of using cDNA labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell. Furthermore, labeling with more than two colors is also contemplated in the present invention. In some embodiments of the invention, at least 5, 10, 20, or 100 dyes of different colors can be used for labeling. Such labeling permits simultaneous hybridizing of the distinguishably labeled cDNA populations to the same array, and thus measuring, and optionally comparing the expression levels of, mRNA molecules derived from more than two samples. Dyes that can be used include, but are not limited to, fluorescein and its derivatives, rhodamine and its derivatives, texas red, 5 carboxy-fluorescein ("FMA"), 2,7-dimethoxy-4,5-dichloro-6-carboxy-fluorescein ("JOE"), N,N,N',N'-tetramethyl-6-carboxy-rhodamine ("TAMRA"), 6 carboxy-X-rhodamine ("ROX"), HEX, TET, IRD40, and IRD41, cyamine dyes, including but are not limited to Cy3, Cy3.5 and Cy5; BODIPY dyes including but are not limited to BODIPY-FL, BODIPY-TR, BODIPY-TMR, BODIPY-630/650, and BODIPY-650/670; and ALEXA dyes, including but are not limited to ALEXA-488, ALEXA-532, ALEXA-546, ALEXA-568, and ALEXA-594; as well as other fluorescent dyes which will be known to those who are skilled in the art.

In some embodiments of the invention, hybridization data are measured at a plurality of different hybridization times so that the evolution of hybridization levels to equilibrium can be determined. In such embodiments, hybridization levels are most preferably measured at hybridization times spanning the range from zero to in excess of what is required for sampling of the bound polynucleotides (i.e., the probe or probes) by the labeled polynucleotides so that the mixture is close to equilibrium, and duplexes are at concentrations dependent on affinity and abundance rather than diffusion. However, the hybridization times are preferably short enough that irreversible binding interactions between the labeled polynucleotide and the probes and/or the surface do not occur, or are at least limited. For example, in embodiments wherein polynucleotide arrays are used to probe a complex mixture of fragmented polynucleotides, typical hybridization times may be approximately 0-72 hours. Appropriate hybridization times for other embodiments will depend on the particular polynucleotide sequences and probes used, and may be determined by those skilled in the art (see, e.g., Sambrook et al., Eds., 1989, *Molecular Cloning: A Laboratory Manual,* 2nd ed., Vol. 1-3, Cold Spring Harbor Laboratory, Cold Spring Harbor, N.Y.).

In one embodiment, hybridization levels at different hybridization times are measured separately on different, identical microarrays. For each such measurement, at hybridization time when hybridization level is measured, the microarray is washed briefly, preferably in room temperature in an aqueous solution of high to moderate salt concentration (e.g., 0.5 to 3 M salt concentration) under conditions which retain all bound or hybridized polynucleotides while removing all unbound polynucleotides. The detectable label on the remaining, hybridized polynucleotide molecules on each probe is then measured by a method which is appropriate to the particular labeling method used. The resulted hybridization levels are then combined to form a hybridization curve. In another embodiment, hybridization levels are measured in real time using a single microarray. In this embodiment, the microarray is allowed to hybridize to the sample without interruption and the microarray is interrogated at each hybridization time in a non-invasive manner. In still another embodiment, one can use one array, hybridize for a short time, wash and measure the hybridization level, put back to the same sample, hybridize for another period of time, wash and measure again to get the hybridization time curve.

Preferably, at least two hybridization levels at two different hybridization times are measured, a first one at a hybridization time that is close to the time scale of cross-hybridization equilibrium and a second one measured at a hybridization time that is longer than the first one. The time scale of cross-hybridization equilibrium depends, inter alia, on sample composition and probe sequence and may be determined by one skilled in the art. In preferred embodiments, the first hybridization level is measured at between 1 to 10 hours, whereas the second hybridization time is measured at 2, 4, 6, 10, 12, 16, 18, 48 or 72 times as long as the first hybridization time.

5.5.1.1 Preparing Probes for Microarrays

As noted above, the "probe" to which a particular polynucleotide molecule, such as an exon, specifically hybridizes according to the invention is a complementary polynucleotide sequence. Preferably one or more probes are selected for each target exon. For example, when a minimum number of probes are to be used for the detection of an exon, the probes normally comprise nucleotide sequences greater than 40 bases in length. Alternatively, when a large set of redundant probes is to be used for an exon, the probes normally comprise nucleotide sequences of 40-60 bases. The probes can also comprise sequences complementary to full length exons. The lengths of exons can range from less than 50 bases to more than 200 bases. Therefore, when a probe length longer than an exon is to be used, it is preferable to augment the exon sequence with adjacent constitutively spliced exon sequences such that the probe sequence is complementary to the continuous mRNA fragment that contains the target exon. This will allow comparable hybridization stringency among the probes of an exon profiling array. It will be understood that each probe sequence may also comprise linker sequences in addition to the sequence that is complementary to its target sequence.

The probes can comprise DNA or DNA "mimics" (e.g., derivatives and analogues) corresponding to a portion of each exon of each gene in an organism's genome. In one embodiment, the probes of the microarray are complementary RNA or RNA mimics. DNA mimics are polymers composed of subunits capable of specific, Watson-Crick-like hybridization with DNA, or of specific hybridization with RNA. The nucleic acids can be modified at the base moiety, at the sugar moiety, or at the phosphate backbone. Exemplary DNA mimics include, e.g., phosphorothioates. DNA can be obtained, e.g., by polymerase chain reaction (PCR) amplification of exon segments from genomic DNA, cDNA (e.g., by RT-PCR), or cloned sequences. PCR primers are preferably chosen based on known sequence of the exons or cDNA that result in amplification of unique fragments (e.g., fragments that do not share more than 10 bases of contiguous identical sequence with any other fragment on the microarray). Computer programs that are well known in the art are useful in the design of primers with the required specificity and optimal amplification properties, such as Oligo version 5.0 (National Biosciences). Typically each probe on the microarray will be between 20 bases and 600 bases, and usually between 30 and 200 bases in length. PCR methods are well known in the art, and are described, for example, in Innis et al., eds., 1990, *PCR Protocols: A Guide to Methods and Applications*, Academic Press Inc., San Diego, Calif. It will be apparent to one skilled in the art that controlled robotic systems are useful for isolating and amplifying nucleic acids.

An alternative, preferred means for generating the polynucleotide probes of the microarray is by synthesis of synthetic polynucleotides or oligonucleotides, e.g., using N-phosphonate or phosphoramidite chemistries (Froehler et al., 1986, *Nucleic Acid Res.* 14:5399-5407; McBride et al., 1983, *Tetrahedron Lett.* 24:246-248). Synthetic sequences are typically between 15 and 600 bases in length, more typically between 20 and 100 bases, most preferably between 40 and 70 bases in length. In some embodiments, synthetic nucleic acids include non-natural bases, such as, but by no means limited to, inosine. As noted above, nucleic acid analogues may be used as binding sites for hybridization. An example of a suitable nucleic acid analogue is peptide nucleic acid (see, e.g., Egholm et al., 1993, *Nature* 363:566-568; and U.S. Pat. No. 5,539,083).

In alternative embodiments, the hybridization sites (i.e., the probes) are made from plasmid or phage clones of genes, cDNAs (e.g., expressed sequence tags), or inserts therefrom (Nguyen et al., 1995, *Genomics* 29:207-209).

5.5.1.2. Attaching Nucleic Acids to the Solid Surface

Preformed polynucleotide probes can be deposited on a support to form the array. Alternatively, polynucleotide probes can be synthesized directly on the support to form the array. The probes are attached to a solid support or surface, which may be made, e.g., from glass, plastic (e.g., polypropylene, nylon), polyacrylamide, nitrocellulose, gel, or other porous or nonporous material.

A preferred method for attaching the nucleic acids to a surface is by printing on glass plates, as is described generally by Schena et al., 1995, *Science* 270:467-470. This method is especially useful for preparing microarrays of cDNA (See also, DeRisi et al, 1996, *Nature Genetics* 14:457-460; Shalon et al., 1996, *Genome Res.* 6:639-645; and Schena et al., 1995, *Proc. Natl. Acad. Sci. U.S.A.* 93:10539-11286).

A second preferred method for making microarrays is by making high-density polynucleotide arrays. Techniques are known for producing arrays containing thousands of oligonucleotides complementary to defined sequences, at defined locations on a surface using photolithographic techniques for synthesis in situ (see, Fodor et al., 1991, *Science* 251:767-773; Lockhart et al., 1996, *Nature Biotechnology* 14:1675; U.S. Pat. Nos. 5,578,832; 5,556,752; and 5,510,270) or other methods for rapid synthesis and deposition of defined oligonucleotides (Blanchard et al., *Biosensors & Bioelectronics* 11:687-690). When these methods are used, oligonucleotides (e.g., 60-mers) of known sequence are synthesized directly on a surface such as a derivatized glass slide. The array produced can be redundant, with several polynucleotide molecules per exon.

Other methods for making microarrays, e.g., by masking (Maskos and Southern, 1992, *Nucl. Acids. Res.* 20:1679-1684), may also be used. In principle, and as noted supra, any type of array, for example, dot blots on a nylon hybridization membrane (see Sambrook et al., supra) could be used. However, as will be recognized by those skilled in the art, very small arrays will frequently be preferred because hybridization volumes will be smaller.

In a particularly preferred embodiment, microarrays of the invention are manufactured by means of an ink jet printing device for oligonucleotide synthesis, e.g., using the methods and systems described by Blanchard in International Patent Publication No. WO 98/41531, published Sep. 24, 1998; Blanchard et al., 1996, *Biosensors and Bioelectronics* 11:687-690; Blanchard, 1998, in *Synthetic DNA Arrays in Genetic Engineering*, Vol. 20, J. K. Setlow, Ed., Plenum Press, New York at pages 111-123; and U.S. Pat. No. 6,028,189 to Blanchard. Specifically, the polynucleotide probes in such microarrays are preferably synthesized in arrays, e.g., on a glass slide, by serially depositing individual nucleotide bases in "microdroplets" of a high surface tension solvent such as propylene carbonate. The microdroplets have small volumes (e.g., 100 µL or less, more preferably 50 µL or less) and are separated from each other on the microarray (e.g., by hydrophobic domains) to form circular surface tension wells that define the locations of the array elements (e.g., the different probes). Polynucleotide probes are normally attached to the surface covalently at the 3 end of the polynucleotide. Alternatively, polynucleotide probes can be attached to the surface covalently at the 5' end of the polynucleotide (see for example, Blanchard, 1998, in *Synthetic DNA Arrays in Genetic Engineering* 20, Setlow, Ed., Plenum Press, New York at pages 111-123).

5.5.1.3. Target Polynucleotide Molecules

Target polynucleotides that can be analyzed by the methods and compositions of the invention include RNA molecules such as, but by no means limited to, messenger RNA (mRNA) molecules, ribosomal RNA (rRNA) molecules, cRNA molecules (i.e., RNA molecules prepared from cDNA molecules that are transcribed in vivo) and fragments thereof. Target polynucleotides which may also be analyzed by the methods and compositions of the present invention include, but are not limited to DNA molecules such as genomic DNA molecules, cDNA molecules, and fragments thereof including oligonucleotides, ESTs, STSs, etc.

The target polynucleotides can be from any source. For example, the target polynucleotide molecules may be naturally occurring nucleic acid molecules such as genomic or extragenomic DNA molecules isolated from an organism, or RNA molecules, such as mRNA molecules, isolated from an organism. Alternatively, the polynucleotide molecules may be synthesized, including, e.g., nucleic acid molecules synthesized enzymatically in vivo or in vitro, such as cDNA molecules, or polynucleotide molecules synthesized by PCR, RNA molecules synthesized by in vitro transcription, etc. The sample of target polynucleotides can comprise, e.g., molecules of DNA, RNA, or copolymers of DNA and RNA. In preferred embodiments, the target polynucleotides of the invention will correspond to particular genes or to particular gene transcripts (e.g., to particular mRNA sequences expressed in cells or to particular cDNA sequences derived from such mRNA sequences). However, in many embodiments, particularly those embodiments wherein the polynucleotide molecules are derived from mammalian cells, the target polynucleotides may correspond to particular fragments of a gene transcript. For example, the target polynucleotides may correspond to different exons of the same gene, e.g., so that different splice variants of that gene may be detected and/or analyzed.

In preferred embodiments, the target polynucleotides to be analyzed are prepared in vitro from nucleic acids extracted from cells. For example, in one embodiment, RNA is extracted from cells (e.g., total cellular RNA, poly(A)$^+$ messenger RNA, or fraction thereof) and messenger RNA is purified from the total extracted RNA. Methods for preparing total and poly(A)$^+$ RNA are well known in the art and are described generally, e.g., in Sambrook et al., supra. In one embodiment, RNA is extracted from cells of the various types of interest in this invention using guanidinium thiocyanate lysis followed by CsCl centrifugation and an oligo dT purification (Chirgwin et al., 1979, *Biochemistry* 18:5294-5299). In another embodiment, RNA is extracted from cells using guanidinium thiocyanate lysis followed by purification on RNeasy columns (Qiagen). The cDNA is then synthesized from the purified mRNA using, e.g., oligo-dT or random primers. In preferred embodiments, the target polynucleotides are cRNA prepared from purified messenger RNA extracted from cells. As used herein, cRNA is defined here as RNA complementary to the source RNA. The extracted RNAs are amplified using a process in which doubled-stranded cDNAs are synthesized from the RNAs using a primer linked to an RNA polymerase promoter in a direction capable of directing transcription of anti-sense RNA. Anti-sense RNAs or cRNAs are then transcribed from the second strand of the double-stranded cDNAs using an RNA polymerase (see, e.g., U.S. Pat. Nos. 5,891,636; 5,716,785; 5,545, 522 and 6,132,997; see also, U.S. Pat. No. 6,271,002, and U.S. Provisional Patent Application Ser. No. 60/253,641, filed on Nov. 28, 2000, by Ziman et al.). Both oligo-dT primers (U.S. Pat. Nos. 5,545,522 and 6,132,997) or random primers (U.S. Provisional Patent Application Ser. No. 60/253,641, filed on Nov. 28, 2000, by Ziman et al.) that contain an RNA polymerase promoter or complement thereof can be used. Preferably, the target polynucleotides are short and/or fragmented polynucleotide molecules which are representative of the original nucleic acid population of the cell.

The target polynucleotides to be analyzed by the methods and compositions of the invention are preferably detectably labeled. For example, cDNA can be labeled directly, e.g., with nucleotide analogs, or indirectly, e.g., by making a second, labeled cDNA strand using the first strand as a template. Alternatively, the double-stranded cDNA can be transcribed into cRNA and labeled.

Preferably, the detectable label is a fluorescent label, e.g., by incorporation of nucleotide analogs. Other labels suitable for use in the present invention include, but are not limited to, biotin, imminobiotin, antigens, cofactors, dinitrophenol, lipoic acid, olefinic compounds, detectable polypeptides, electron rich molecules, enzymes capable of generating a detectable signal by action upon a substrate, and radioactive isotopes. Preferred radioactive isotopes include $^{32}$P, $^{35}$S, $^{15}$N and $^{125}$I. Fluorescent molecules suitable for the present invention include, but are not limited to, fluorescein and its derivatives, rhodamine and its derivatives, texas red, 5 carboxyfluorescein ("FMA"), 2,7-dimethoxy-4,5-dichloro-6-carboxy-fluorescein ("JOE"), N,N,N',N'-tetramethyl-6-carboxy-rhodamine ("TAMRA"), 6 carboxy-X-rhodamine ("ROX"), HEX, TET, IRD40, and IRD41. Fluorescent molecules that are suitable for the invention further include: cyamine dyes, including by not limited to Cy3, Cy3.5 and Cy5; BODIPY dyes including but not limited to BODIPY-FL, BODIPY-TR, BODIPY-TMR, BODIPY-630/650, and BODIPY-650/670; and ALEXA dyes, including but not limited to ALEXA-488, ALEXA-532, ALEXA-546, ALEXA-568, and ALEXA-594; as well as other fluorescent dyes which will be known to those who are skilled in the art. Electron rich indicator molecules suitable for the present invention include, but are not limited to, ferritin, hemocyanin, and colloidal gold. Alternatively, in less preferred embodiments the target polynucleotides may be labeled by specifically complexing a first group to the polynucleotide. A second group, covalently linked to an indicator molecules and which has an affinity for the first group, can be used to indirectly detect the target polynucleotide. In such an embodiment, compounds suitable for use as a first group include, but are not limited to, biotin and iminobiotin. Compounds suitable for use as a second group include, but are not limited to, avidin and streptavidin.

5.5.1.4. Hybridization to Microarrays

As described supra, nucleic acid hybridization and wash conditions are chosen so that the polynucleotide molecules to be analyzed by the invention (referred to herein as the "target polynucleotide molecules) specifically bind or specifically hybridize to the complementary polynucleotide sequences of the array, preferably to a specific array site, wherein its complementary DNA is located.

Arrays containing double-stranded probe DNA situated thereon are preferably subjected to denaturing conditions to render the DNA single-stranded prior to contacting with the target polynucleotide molecules. Arrays containing single-stranded probe DNA (e.g., synthetic oligodeoxyribonucleic acids) may need to be denatured prior to contacting with the target polynucleotide molecules, e.g., to remove hairpins or dimers which form due to self complementary sequences.

Optimal hybridization conditions will depend on the length (e.g., oligomer versus polynucleotide greater than 200 bases) and type (e.g., RNA, or DNA) of probe and target nucleic acids. General parameters for specific (i.e., stringent) hybridization conditions for nucleic acids are described in Sambrook et al., (supra), and in Ausubel et al., 1987, *Current Protocols in Molecular Biology*, Greene Publishing and Wiley-Interscience, New York. When the cDNA microarrays of Schena et al. are used, typical hybridization conditions are hybridization in 5×SSC plus 0.2% SDS at 65° C. for four hours, followed by washes at 25° C. in low stringency wash buffer (1×SSC plus 0.2% SDS), followed by 10 minutes at 25° C. in higher stringency wash buffer (0.1×SSC plus 0.2% SDS) (Schena et al., 1996, *Proc. Natl. Acad. Sci. U.S.A.* 93:10614). Useful hybridization conditions are also provided in, e.g., Tijessen, 1993, *Hybridization With Nucleic Acid Probes*, Elsevier Science Publishers B. V. and Kricka, 1992, Nonisotopic DNA Probe Techniques, Academic Press, San Diego, Calif.

Particularly preferred hybridization conditions for use with the screening and/or signaling chips of the present invention include hybridization at a temperature at or near the mean melting temperature of the probes (e.g., within 5° C., more preferably within 2° C.) in 1 M NaCl, 50 mM MES buffer (pH 6.5), 0.5% sodium Sarcosine and 30 percent formamide.

5.5.1.5. Signal Detection and Data Analysis

It will be appreciated that when target sequences, e.g., cDNA or cRNA, complementary to the RNA of a cell is made and hybridized to a microarray under suitable hybridization conditions, the level of hybridization to the site in the array corresponding to an exon of any particular gene will reflect the prevalence in the cell of mRNA or mRNAs containing the exon transcribed from that gene. For example, when detectably labeled (e.g., with a fluorophore) cDNA complementary to the total cellular mRNA is hybridized to a microarray, the site on the array corresponding to an exon of a gene (i.e., capable of specifically binding the product or products of the gene expressing) that is not transcribed or is removed during RNA splicing in the cell will have little or no signal (e.g., fluorescent signal), and an exon of a gene for which the encoded mRNA expressing the exon is prevalent will have a relatively strong signal. The relative abundance of different mRNAs produced from the same gene by alternative splicing is then determined by the signal strength pattern across the whole set of exons monitored for the gene.

In preferred embodiments, target sequences, e.g., cDNAs or cRNAs, from two different cells are hybridized to the binding sites of the microarray. In the case of drug responses one cell sample is exposed to a drug and another cell sample of the same type is not exposed to the drug. In the case of pathway responses one cell is exposed to a pathway perturbation and another cell of the same type is not exposed to the pathway perturbation. The cDNA or cRNA derived from each of the two cell types are differently labeled so that they can be distinguished. In one embodiment, for example, cDNA from a cell treated with a drug (or exposed to a pathway perturbation) is synthesized using a fluorescein-labeled dNTP, and cDNA from a second cell, not drug-exposed, is synthesized using a rhodamine-labeled dNTP. When the two cDNAs are mixed and hybridized to the microarray, the relative intensity of signal from each cDNA set is determined for each site on the array, and any relative difference in abundance of a particular exon detected.

In the example described above, the cDNA from the drug-treated (or pathway perturbed) cell will fluoresce green when the fluorophore is stimulated and the cDNA from the untreated cell will fluoresce red. As a result, when the drug treatment has no effect, either directly or indirectly, on the transcription and/or post-transcriptional splicing of a particular gene in a cell, the exon expression patterns will be indistinguishable in both cells and, upon reverse transcription, red-labeled and green-labeled cDNA will be equally prevalent. When hybridized to the microarray, the binding site(s) for that species of RNA will emit wavelengths characteristic of both fluorophores. In contrast, when the drug-exposed cell is treated with a drug that, directly or indirectly, changes the transcription and/or post-transcriptional splicing of a particular gene in the cell, the exon expression pattern as represented by ratio of green to red fluorescence for each exon binding site will change. When the drug increases the prevalence of an mRNA, the ratios for each exon expressed in the mRNA will increase, whereas when the drug decreases the prevalence of an mRNA, the ratio for each exon expressed in the mRNA will decrease.

The use of a two-color fluorescence labeling and detection scheme to define alterations in gene expression has been described in connection with detection of mRNAs, e.g., in Schena et al., 1995, Science 270:467-470, which is incorporated by reference in its entirety for all purposes. The scheme is equally applicable to labeling and detection of exons. An advantage of using target sequences, e.g., cDNAs or cRNAs, labeled with two different fluorophores is that a direct and internally controlled comparison of the mRNA or exon expression levels corresponding to each arrayed gene in two cell states can be made, and variations due to minor differences in experimental conditions (e.g., hybridization conditions) will not affect subsequent analyses. However, it will be recognized that it is also possible to use cDNA from a single cell, and compare, for example, the absolute amount of a particular exon in, e.g., a drug-treated or pathway-perturbed cell and an untreated cell.

When fluorescently labeled probes are used, the fluorescence emissions at each site of a transcript array can be, preferably, detected by scanning confocal laser microscopy. In one embodiment, a separate scan, using the appropriate excitation line, is carried out for each of the two fluorophores used. Alternatively, a laser can be used that allows simultaneous specimen illumination at wavelengths specific to the two fluorophores and emissions from the two fluorophores can be analyzed simultaneously (see Shalon et al., 1996, *Genome Res.* 6:639-645). In a preferred embodiment, the arrays are scanned with a laser fluorescence scanner with a computer controlled X-Y stage and a microscope objective. Sequential excitation of the two fluorophores is achieved with a multi-line, mixed gas laser, and the emitted light is split by wavelength and detected with two photomultiplier tubes. Such fluorescence laser scanning devices are described, e.g., in Schena et al., 1996, *Genome Res.* 6:639-645. Alternatively, the fiber-optic bundle described by Ferguson et al., 1996, *Nature Biotech.* 14:1681-1684, may be used to monitor mRNA abundance levels at a large number of sites simultaneously.

Signals are recorded and, in a preferred embodiment, analyzed by computer, e.g., using a 12 bit analog to digital board. In one embodiment, the scanned image is despeckled using a graphics program (e.g., Hijaak Graphics Suite) and then analyzed using an image gridding program that creates a spreadsheet of the average hybridization at each wavelength at each site. If necessary, an experimentally determined correction for "cross talk" (or overlap) between the channels for the two fluors can be made. For any particular hybridization site on the transcript array, a ratio of the emission of the two fluorophores can be calculated. The ratio is independent of the absolute expression level of the cognate gene, but is useful for genes whose expression is significantly modulated by drug administration, gene deletion, or any other tested event.

According to the method of the invention, the relative abundance of an mRNA and/or an exon expressed in an mRNA in two cells or cell lines is scored as perturbed (i.e., the abundance is different in the two sources of mRNA tested) or as not perturbed (i.e., the relative abundance is the same). As used herein, a difference between the two sources of RNA of at least a factor of 25 percent (e.g., RNA is 25 more abundant in one source than in the other source), more usually 50 percent, even more often by a factor of 2 (e.g., twice as abundant), 3 (three times as abundant), or 5 (five times as abundant) is scored as a perturbation. Present detection methods allow reliable detection of differences of an order of 1.5 fold to 3-fold.

It is, however, also advantageous to determine the magnitude of the relative difference in abundances for an mRNA and/or an exon expressed in an mRNA in two cells or in two cell lines. This can be carried out, as noted above, by calculating the ratio of the emission of the two fluorophores used for differential labeling, or by analogous methods that will be readily apparent to those of skill in the art.

5.5.2 Other Methods of Transcriptional State Measurement

The transcriptional state of a cell can be measured by other gene expression technologies known in the art. Several such technologies produce pools of restriction fragments of limited complexity for electrophoretic analysis, such as methods combining double restriction enzyme digestion with phasing primers (see, e.g., European Patent 534858 A1, filed Sep. 24, 1992, by Zabeau et al.), or methods selecting restriction fragments with sites closest to a defined mRNA end (see, e.g., Prashar et al., 1996, *Proc. Natl. Acad. Sci. USA* 93:659-663). Other methods statistically sample cDNA pools, such as by sequencing sufficient bases (e.g., 20-50 bases) in each of multiple cDNAs to identify each cDNA, or by sequencing short tags (e.g., 9-10 bases) that are generated at known positions relative to a defined mRNA end (see, e.g., Velculescu, 1995, *Science* 270:484-487).

The transcriptional state of a cell can also be measured by reverse transcription-polymerase chain reaction (RT-PCR). RT-PCR is a technique for mRNA detection and quantitation. RT-PCR is sensitive enough to enable quantitation of RNA from a single cell. See, for example, Pfaffl and Hageleit, 2001, Biotechnology Letters 23, 275-282; Tadesse et al., 2003, Mol Genet Genomics 269, p. 789-796; and Kabir and Shimizu, 2003, J. Biotech. 9, p. 105.

5.6 Measurement of Other Aspects of the Biological State

In various embodiments of the present invention, aspects of the biological state other than the transcriptional state, such as the translational state, the activity state, or mixed aspects can be measured. Thus, in such embodiments, cellular constituent abundance data can include translational state measurements or even protein expression measurements. Details of aspects of the biological state other than the transcriptional state are described in this section.

5.6.1 Translational State Measurements

Measurement of the translational state can be performed according to several methods. For example, whole genome monitoring of protein (e.g., the "proteome,") can be carried out by constructing a microarray in which binding sites comprise immobilized, preferably monoclonal, antibodies specific to a plurality of protein species encoded by the cell genome. Preferably, antibodies are present for a substantial fraction of the encoded proteins, or at least for those proteins relevant to the action of a drug of interest. Methods for making monoclonal antibodies are well known (see, e.g., Harlow and Lane, 1988, *Antibodies: A Laboratory Manual*, Cold Spring Harbor, N.Y., which is incorporated in its entirety for all purposes). In one embodiment, monoclonal antibodies are raised against synthetic peptide fragments designed based on genomic sequence of the cell. With such an antibody array, proteins from the cell are contacted to the array and their binding is assayed with assays known in the art.

Alternatively, proteins can be separated by two-dimensional gel electrophoresis systems. Two-dimensional gel electrophoresis is well-known in the art and typically involves iso-electric focusing along a first dimension followed by SDS-PAGE electrophoresis along a second dimension. See, e.g., Hames et al., 1990, *Gel Electrophoresis of Proteins: A Practical Approach*, IRL Press, New York; Shevchenko et al., 1996, *Proc. Natl. Acad. Sci. USA* 93:1440-1445; Sagliocco et al., 1996, Yeast 12:1519-1533; Lander, 1996, *Science* 274: 536-539. The resulting electropherograms can be analyzed by numerous techniques, including mass spectrometric techniques, Western blotting and immunoblot analysis using polyclonal and monoclonal antibodies, and internal and N-terminal micro-sequencing. Using these techniques, it is possible to identify a substantial fraction of all the proteins produced under given physiological conditions, including in cells (e.g., in yeast) exposed to a drug, or in cells modified by, e.g., deletion or over-expression of a specific gene.

5.6.2 Other Types of Cellular Constituent Abundance Measurements

The methods of the invention are applicable to any cellular constituent that can be monitored. For example, where activities of proteins can be measured, embodiments of this invention can use such measurements. Activity measurements can be performed by any functional, biochemical, or physical means appropriate to the particular activity being characterized. Where the activity involves a chemical transformation, the cellular protein can be contacted with the natural substrate(s), and the rate of transformation measured. Where the activity involves association in multimeric units, for example association of an activated DNA binding complex with DNA, the amount of associated protein or secondary consequences of the association, such as amounts of mRNA transcribed, can be measured. Also, where only a functional activity is known, for example, as in cell cycle control, performance of the function can be observed. However known and measured, the changes in protein activities form the response data analyzed by the foregoing methods of this invention.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry, is provided. Each unique chemistry is designed to test a particular phenotype. Cells from the organism of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes can be recorded as often as several times each hour. During one incubation, more than 5,000 phenotypes can be tested. See, for example, Bochner et al., 2001, Genome Research 11, p. 1246.

In some embodiments of the present invention, cellular constituent measurements are derived from cellular phenotypic techniques. One such cellular phenotypic technique uses cell respiration as a universal reporter. In one embodiment, 96-well microtiter plates, in which each well contains its own unique chemistry is provided. Each unique chemistry is designed to test a particular phenotype. Cells from biological specimens of interest are pipetted into each well. If the cells exhibit the appropriate phenotype, they will respire and actively reduce a tetrazolium dye, forming a strong purple color. A weak phenotype results in a lighter color. No color means that the cells don't have the specific phenotype. Color changes may be recorded as often as several times each hour. During one incubation, more than 5,000 phenotypes can be tested. See, for example, Bochner et al., 2001, Genome Research 11, 1246-55.

In some embodiments of the present invention, the cellular constituents that are measured are metabolites. Metabolites include, but are not limited to, amino acids, metals, soluble sugars, sugar phosphates, and complex carbohydrates. Such metabolites can be measured, for example, at the whole-cell level using methods such as pyrolysis mass spectrometry (Irwin, 1982, *Analytical Pyrolysis: A Comprehensive Guide*, Marcel Dekker, New York; Meuzelaar et al., 1982, *Pyrolysis Mass Spectrometry of Recent and Fossil Biomaterials*, Elsevier, Amsterdam), fourier-transform infrared spectrometry (Griffiths and de Haseth, 1986, Fourier transform infrared spectrometry, John Wiley, New York; Helm et al., 1991, J. Gen. Microbiol. 137, 69-79; Naumann et al., 1991, Nature 351, 81-82; Naumann et al., 1991, In: *Modern techniques for rapid microbiological analysis*, 43-96, Nelson, W. H., ed., VCH Publishers, New York), Raman spectrometry, gas chromatography-mass spectroscopy (GC-MS) (Fiehn et al., 2000, Nature Biotechnology 18, 1157-1161, capillary electrophoresis (CE)/MS, high pressure liquid chromatography/mass spectroscopy (HPLC/MS), as well as liquid chromatography (LC)-Electrospray and cap-LC-tandem-electrospray mass spectrometries. Such methods can be combined with established chemometric methods that make use of artificial neural networks and genetic programming in order to discriminate between closely related samples.

5.7 Analytic Kit Implementation

In one embodiment, the methods of this invention can be implemented by use of kits for developing and using biological classifiers. Such kits contain microarrays, such as those described in subsections above. The microarrays contained in such kits comprise a solid phase, e.g., a surface, to which probes are hybridized or bound at a known location of the solid phase. Preferably, these probes consist of nucleic acids of known, different sequence, with each nucleic acid being capable of hybridizing to an RNA species or to a cDNA species derived therefrom. In a particular embodiment, the probes contained in the kits of this invention are nucleic acids capable of hybridizing specifically to nucleic acid sequences derived from RNA species in cells collected from an organism of interest.

In a preferred embodiment, a kit of the invention also contains one or more data structures and/or software modules described above and in FIGS. 1-3 and/or 5, encoded on computer readable medium, and/or an access authorization to use the databases described above from a remote networked computer.

In another preferred embodiment, a kit of the invention contains software capable of being loaded into the memory of a computer system such as the one described supra, and illustrated in FIG. 1. The software contained in the kit of this invention, is essentially identical to the software described above in conjunction with FIG. 1.

Alternative kits for implementing the analytic methods of this invention will be apparent to one of skill in the art and are intended to be comprehended within the accompanying claims.

6. REFERENCES CITED

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a computer readable storage medium. For instance, the computer program product could contain the program modules shown in FIG. 1 and/or the database schema shown in FIGS. 2 and 3. These program modules can be stored on a CD-ROM, magnetic disk storage product, or any other computer readable data or program storage product. The software modules in the computer program product can also be distributed electronically, via the Internet or otherwise, by transmission of a computer data signal (in which the software modules are embedded) on a carrier wave.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:
1. A method comprising:
receiving data, wherein said data comprises one or more characteristics for each cellular constituent in a plurality of cellular constituents that have been measured in a single biological specimen from a patient;
applying a plurality of pre-trained models using said data to produce a model score for each respective pre-trained model in said plurality of pre-trained models thereby obtaining a plurality of model scores, wherein each model score in the plurality of model scores is a number that represents the likelihood of a corresponding biological feature represented by the corresponding model being present in the patient, wherein prior to applying the plurality of pre-trained models it is deemed unknown whether the patient has the corresponding biological feature, wherein applying a respective model in said plurality of models comprises determining the model score for the respective model using one or more characteristics for a sub-plurality of cellular constituents in said plurality of cellular constituents in said data that have been measured in the patient, the plurality of pre-trained models comprising a first pre-trained model using one or more characteristics of a first sub-plurality of cellular constituents in said plurality of cellular constituents and a second pre-trained model using one or more characteristics of a second sub-plurality of cellular constituents in said plurality of cellular constituents, wherein the first sub-plurality of cellular constituents includes at least one cellular constituent that is not present in the second sub-plurality of cellular constituents;

communicating said plurality of model scores; and treating the patient for a biological feature associated with a model score representing that there is a high likelihood the biological feature is present in the patient.

2. The method of claim 1, wherein:
said one or more characteristics are abundances;
said cellular constituents are mRNAs;
said applying said plurality of pre-trained models comprises determining said model score for each respective model using said abundances of more than 500 mRNAs in said plurality of cellular constituents that have been measured in said biological specimen;
said biological features comprise biological features that are different diseases; and
said different diseases are each a primary tumor site of origin.

3. The method of claim 2, wherein said more than 500 mRNAs are more than 1000 mRNAs.

4. The method of claim 2, wherein said primary tumor sites of origin are selected from the group consisting of prostate, breast, colorectum, lung, liver, gastroesophagus, pancreas, ovary, kidney, and bladder/ureter.

5. The method of claim 2, wherein the patient is human.

6. The method of claim 1, wherein said plurality of pre-trained models collectively represent the independent likelihoods of two or more biological features wherein at least one of said biological features is a disease and at least one of said biological features is sensitivity to a drug.

7. The method of claim 1, wherein
a model precondition is included within a first pre-trained model in the plurality of pre-trained models, and
applying the plurality of pre-trained models comprises determining whether the model precondition has been satisfied, wherein satisfaction of the model precondition for the first pre-trained model requires a second pre-trained model in the plurality of pre-trained models to have a specific predetermined model score, and wherein the first pre-trained model is applied when the model precondition is satisfied and the first pre-trained model is not applied when the model precondition is not satisfied.

8. The method of claim 1, wherein said biological feature is a disease.

9. The method of claim 1, wherein the patient is human.

10. The method of claim 1, wherein said one or more characteristics comprises cellular constituent abundance and said data comprises cellular constituent abundances of at least one hundred cellular constituents in the biological specimen from the patient.

11. The method of claim 1, wherein said one or more characteristics comprises cellular constituent abundance and said data comprises cellular constituent abundances of at least five hundred cellular constituents in the biological specimen from the patient.

12. The method of claim 1, wherein said one or more characteristics comprises cellular constituent abundance and said data comprises cellular constituent abundances of between one thousand and twenty thousand cellular constituents in the biological specimen from the patient.

13. The method of claim 1, wherein said biological feature is sensitivity to a drug.

14. The method of claim 1, wherein the plurality of pre-trained models collectively represent the likelihood of each of five or more biological features.

15. The method of claim 1, wherein each biological feature in said five or more biological features is a cancer origin.

16. The method of claim 1, wherein the steps of receiving data, applying a plurality of pre-trained models, and communicating said plurality of model scores are performed at a system comprising one or more processors and memory.

17. The method of claim 1, wherein treating the patient comprises administering a drug to the patient.

18. The method of claim 1, wherein treating the patient comprises administering a combination of drugs to the patient.

* * * * *